US008865723B2

(12) United States Patent
Gurney et al.

(10) Patent No.: US 8,865,723 B2
(45) Date of Patent: Oct. 21, 2014

(54) SELECTIVE PDE4 B INHIBITION AND IMPROVEMENT IN COGNITION IN SUBJECTS WITH BRAIN INJURY

(71) Applicant: Tetra Discovery Partners LLC, Grand Rapids, MI (US)

(72) Inventors: Mark E. Gurney, Grand Rapids, MI (US); Coleen M. Atkins, Miami, FL (US); David J. Adaikkalasamy, Miami, FL (US); W. Dalton Dietrich, Miami, FL (US)

(73) Assignee: Tetra Discovery Partners LLC, Grand Rapids, MI (US)

( * ) Notice: Subject to any disclaimer, the term of this patent is extended or adjusted under 35 U.S.C. 154(b) by 0 days.

(21) Appl. No.: 13/799,505

(22) Filed: Mar. 13, 2013

(65) Prior Publication Data
US 2014/0121221 A1 May 1, 2014

Related U.S. Application Data

(60) Provisional application No. 61/718,581, filed on Oct. 25, 2012.

(51) Int. Cl.
*A01N 43/54* (2006.01)
*C07D 239/42* (2006.01)
*C07D 401/04* (2006.01)
*C07D 401/00* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)
*A61K 31/506* (2006.01)
*A61K 31/505* (2006.01)

(52) U.S. Cl.
CPC .............. *A61K 31/506* (2013.01); *A61K 31/505* (2013.01)
USPC .......................................... 514/256; 544/328

(58) Field of Classification Search
CPC . A61K 31/136; A61K 31/192; A61K 31/216; A61K 31/381; A61K 31/505; A61K 31/506; C07D 233/96; C07D 333/04
USPC .......................................... 514/256; 544/328
See application file for complete search history.

(56) References Cited

U.S. PATENT DOCUMENTS

| | | | |
|---|---|---|---|
| 7,326,729 B2 | 2/2008 | Chao et al. | |
| 7,511,062 B2 | 3/2009 | Kuang et al. | |
| 7,691,856 B2 | 4/2010 | Taveras et al. | |
| 7,928,132 B2 | 4/2011 | Kohn et al. | |
| 7,960,433 B2 | 6/2011 | Taveras et al. | |
| 2003/0045533 A1 | 3/2003 | Liu et al. | |
| 2004/0053953 A1 | 3/2004 | Taveras et al. | |
| 2004/0186142 A1 | 9/2004 | Taveras et al. | |
| 2006/0014794 A1 | 1/2006 | Chao et al. | |
| 2006/0025453 A1 | 2/2006 | Taveras et al. | |
| 2006/0106062 A1 | 5/2006 | Kuang et al. | |
| 2006/0106085 A1 | 5/2006 | Zeldis et al. | |
| 2006/0293343 A1 | 12/2006 | Naganuma et al. | |
| 2007/0155739 A1 | 7/2007 | Sucholeiki et al. | |
| 2008/0045489 A1 | 2/2008 | Chao et al. | |
| 2008/0090823 A1 | 4/2008 | Biju et al. | |
| 2008/0132505 A1 | 6/2008 | Brown et al. | |
| 2008/0260751 A1 | 10/2008 | Karp et al. | |
| 2008/0261977 A1 | 10/2008 | Eatherton et al. | |
| 2008/0279822 A1 | 11/2008 | Hu et al. | |
| 2008/0280868 A1 | 11/2008 | Eatherton et al. | |
| 2009/0130077 A1* | 5/2009 | Singh et al. ................... 424/94.1 |
| 2009/0136473 A1 | 5/2009 | Singh et al. | |
| 2009/0324569 A1 | 12/2009 | Singh et al. | |
| 2010/0010020 A1 | 1/2010 | Liu et al. | |
| 2011/0110957 A1 | 5/2011 | Stamford et al. | |
| 2012/0148603 A1 | 6/2012 | Stamford et al. | |
| 2012/0183563 A1 | 7/2012 | Scott et al. | |
| 2012/0189642 A1 | 7/2012 | Scott et al. | |
| 2012/0195881 A1 | 8/2012 | Iserloh et al. | |
| 2012/0213758 A1 | 8/2012 | Singh et al. | |

FOREIGN PATENT DOCUMENTS

| | | |
|---|---|---|
| EP | 2377533 A2 | 10/2011 |
| WO | WO-02/098878 A1 | 12/2002 |
| WO | WO-03/080053 A1 | 10/2003 |
| WO | WO-2004/033440 A1 | 4/2004 |
| WO | WO-2005/113534 A2 | 12/2005 |
| WO | WO-2005/116009 A1 | 12/2005 |
| WO | WO-2006/123639 A1 | 11/2006 |
| WO | WO-2007/079199 A2 | 7/2007 |
| WO | WO-2008/005570 A1 | 1/2008 |
| WO | WO-2009/020534 A2 | 2/2009 |
| WO | WO-2009/067600 A2 | 5/2009 |

(Continued)

OTHER PUBLICATIONS

Suzuki et. al., Journal of Medicinal Chemistry, 1993, American Chemical Society, vol. 36, pp. 2508-2518.*
Wishka et. al., Journal of Medicinal Chemistry, 2006, American Chemical Society, vol. 49, pp. 4425-4436.*
Lobaugh et. al., Archives in Pediatric and Adolescent Medicine, 2001, American Medical Association, vol. 155, pp. 442-448.*
Jelic et. al., Acta Neurologica Scandinavia, 2003, Blackwell Munksgaard, vol. 107, supplemental 179, pp. 83-93.*
Ryan et. al., International Review of Psychiatry, Nov. 2003, BrunnerRoutledge, vol. 15, pp. 310-316.*

(Continued)

*Primary Examiner* — Sarah Pihonak
(74) *Attorney, Agent, or Firm* — Marshall, Gerstein & Borun LLP

(57) ABSTRACT

Provided herein are methods of improving cognitive ability or memory in a subject that has suffered a brain injury or spinal cord injury by administering a selective PDE4 B inhibitor.

24 Claims, 2 Drawing Sheets

(56) References Cited

FOREIGN PATENT DOCUMENTS

| WO | WO-2009/067621 A1 | 5/2009 |
|---|---|---|
| WO | WO-2011/006066 A1 | 1/2011 |
| WO | WO-2011/044181 A1 | 4/2011 |
| WO | WO-2011/071996 A1 | 6/2011 |
| WO | WO-2011/100324 A1 | 8/2011 |
| WO | WO-2011/100359 A1 | 8/2011 |
| WO | WO-2012/088431 A1 | 6/2012 |
| WO | WO-2012/088469 A1 | 6/2012 |

OTHER PUBLICATIONS

Atkins et al., Effects of early rolipram treatment on histopathological outcome after controlled cortical impact injury in mice. *Neuro. Lett.*, 532: 1-6 (2013)—Epub Oct. 26, 2013.

Atkins et al., Modulation of the cAMP signaling pathway after traumatic brain injury. *Exp. Neurol.*, 208: 145-58 (2007).

Atkins et al., Postinjury treatment with rolipram increases hemorrhage after traumatic brain injury. *J. Neurosci. Res.*, 90: 1861-71 (2012).

Blokland et al., Improving memory: A role of phosphodiesterases. *Curr. Pharmaceut. Design*, 12: 2511-23 (2006).

Bruno et al., GEBR-7b, a novel PDE4D selective inhibitor that improves memory in rodent at non-emetic doses. *Brit. J. Pharmacol.*, 164: 2054-63 (2011).

Burgin et al., Design of phosphodiesterase 4D (PDE4D) allosteric modulators for enhancing cognition with improved safety. *Nat. Biotechnol.*, 28: 63-70 (2010).

Card et al., Structural basis for the activity of drugs that inhibit phophodiesterases. *Structure*, 12: 2233-47 (2004).

D'Avila et al., Microglial activation induced by brain trauma is suppressed by post-injury treatment with a PARP inhibitor. *J. Neuroinflam.*, 9: 31-41 (2012).

Gandy et al., APOEε4 status and traumatic brain injury on the gridiron or the battlefield. *Sci. Transl. Med.*, 4: 134ed4 (2012).

Ghosh et al., Proinflammatory cytokine regulation of cyclic AMP-phosphodiesterase 4 signaling in microglia in vitro and following CNS injury. *Glia*, 1-21 (2012).

Goldstein et al., Chronic traumatic encephalopathy in blast-exposed military veterans and a blast neurotrauma mouse model. *Sci. Transl. Med.*, 4: 134ra60 (2012).

Houslay et al., Phophodiesterase-4 as a therapeutic target. *Drug Discov. Today*, 10(22): 1503-19 (2005).

Li et al., Phosphodiesterase-4D knock-out and RNA interference-mediated knock-down enhance memory and increase hippocampal neurogenesis via increased cAMP signaling. *J. Neurosci.*, 31: 172-83 (2011).

Maas et al., Efficacy and safety of dexanabinol in severe traumatic brain injury: Result of a phase III randomised, placebo-controlled, clinical trial. *Lancet*, 5: 38-45 (2006).

MacDonald et al., A novel phosphodiesterase type 4 inhibitor, HT-0712, enhances rehabilitation-dependent motor recovery and cortical reorganization after motor recovery and cortical reorganization after focal cortical ischemic. *Neurorehab. Neural Repair*, 21(6): 486-96 (2007).

Naganuma et al., Discovery of selective PDE4B inhibitors. *Bioorg. Med. Chem. Lett.*, 19(12): 3174-6 (2009). Accepted Manuscript.

Oliva et al., Phosphodiesterase isoform-specific expression induced by traumatic brain injury. *J. Neurochem.* E-pub dated Oct. 12, 2012.

Pearse et al., cAMP and Schwann cells promote axonal growth and functional recovery after spinal cord injury. *Nat. Med.*, 10(6): 610-6 (2004).

Press et al., PDE4 inhibitors—A review of the current field. *Prog. Med. Chem.*, 47: 37-74 (2009).

Roberts et al., Effect of intravenous corticosteroids on death within 14 days in 10008 adults with clinically significant head injury (MRC CRASH trial): Randomised placebo-controlled trial. *Lancet*, 1321-8 (2004).

Rutton et al., Selective PDE inhibitors rolipram and sildenafil improve object retrieval performance in adult cynomolgus macaques. *Psychopharmacology*, (2007).

Shohami et al., Cytokine production in the brain following closed head injury: Dexanabinol.(HU-211) is a novel TNF-α inhibitor and an effective neuroprotectant. *J. Neuroimmunol.*, 72: 169-77 (1997).

Siuciak et al., Behavioral and neurochemical characterization of mice deficient in the phosphodiesterase-4B (PDE4B) enzyme. *Psychopharmacology*, (2007).

Titus et al., Phosphodiesterase inhibition rescues chronic cognitive deficits induced by traumatic brain injury. *J. Neurosci.*, 33(12)—to publish Mar. 20, 2013.

Wang et al., RNA interference-mediated phosphodiesterase-4D splice variants knockdown in the prefrontal cortex produces antidepressant-like and cognition-enhancing effects. *Brit. J. Pharmacol.*, 168(4): 1001-14 (2013).

Zhang et al., Anxiogenic-like behavioral phenotype of mice deficient in phosphodiesterase 4B (PDE4B). *Neuropsychopharmacology*, 1-13 (2007).

Zhang et al., Anxiogenic-like behavioral phenotype of mice deficient in phosphodiesterase 4B (PDE4B). *Neuropsychopharmacology*, 33(7): 1611-23 (2008)—Author Manuscript.

Ziebell et al., Involvement of pro- and anti-inflammatory cytokines and chemokines in the pathophysiology of traumatic brain injury. *J. Am. Soc. Exp. Neurother.*, 7: 22-30 (2010).

\* cited by examiner

SELECTIVE PDE4 B INHIBITION AND IMPROVEMENT IN COGNITION IN SUBJECTS WITH BRAIN INJURY

STATEMENT OF U.S. GOVERNMENT SUPPORT

This invention was made with government support under Grant Nos. NS069721; NS056072 and 1R43MH091791 awarded by the National Institutes of Health. The government has certain rights in the invention.

FIELD OF THE INVENTION

The invention pertains to improving cognitive function, sensory function, motor function, or paralysis in a subject that has sustained a brain injury or spinal cord injury and has impairment in one or more of these neurological functions.

BACKGROUND

A significant amount of research has been directed towards measuring damage to cognition, motor function, sensory function, and paralysis in subject suffering from a brain injury or spinal cord injury (SCI), and the mechanisms involved in each. Increased understanding of these mechanisms, and ability to manipulate them, would be of extraordinary scientific interest and practical importance. Cognitive impairment is one of the most common conditions that occurs in subjects suffering from a brain injury or SCI. Such impairment may include a reduction in the ability to learn new information and/or to retrieve information that has previously been learned. Decreased motor or sensory function and paralysis are some of the most common conditions that occurs in SCI subjects. Such loss of function in subjects that have suffered a brain injury or SCI results in decreased quality of life and independence. Often one or more neurological impairments persists after a subject has been treated for the trauma and acute phase of injuries that resulted from the trauma.

At present there is a lack of effective pharmacological methods for improving cognitive impairment, motor function, sensory function, and paralysis in subject suffering from one or more neurological impairments that have resulted from traumatic brain injury, hypoxic event, SCI, or other trauma. A need exists for such materials and methods.

SUMMARY

Provided herein are materials (e.g., compounds and compositions) and methods of improving cognitive function in a mammalian subject with cognitive impairment or improving motor function, sensory function, or paralysis in a mammalian subject. For example, in one embodiment, the invention includes a method of improving cognitive function in a mammalian subject with cognitive impairment or improving motor function, sensory function, or paralysis in a mammalian subject, comprising administering an effective amount of a selective PDE4 B inhibitor to the subject. In some embodiments, brain cells of a mammalian subject are contacted with an effective amount of a selective PDE4 B inhibitor to improve cognitive impairment, motor function, sensory function, or paralysis of the mammalian subject. The selective PDE4 B inhibitor can be formulated in a composition with a pharmaceutically acceptable carrier. Such compositions and their use for the purposes described herein are also embodiments of the invention.

The subject can be human. The subject can have sustained a traumatic brain injury (TBI) or a spinal cord injury. In various cases, the methods disclosed herein further comprise examining the subject with a TBI to determine if cognitive impairment exists. The TBI can be assessed using the Glasgow Coma Scale or Rancho Los Amigos scale. The TBI can have resulted from a closed TBI, a penetrating TBI, proximity or exposure to an explosive blast or blast wind, one or more concussion events or chronic traumatic encephalopathy (CTE), concussion events from repeated head trauma from sports, athletics, or a vehicular accident, a fall or child or domestic abuse, or from a hypoxia event. The hypoxia event can result from a cardiac arrest, a myocardial infarction, a stroke, a near suffocation, a near drowning, during general anesthesia, during cardiac surgery, or during open heart surgery, and can have occurred prenatally or perinatally. In some cases, the subject is substantially free of inflammation due to the TBI prior to the administration of or the contacting with the selective PDE4 B inhibitor.

The improvement to cognitive function can be an improvement in one or more of short term memory, long term memory, attention span, working memory, and/or one or more of improvement with at least one parameter selected from attention span, judgment, processing speed, distractability, abstract reasoning, planning, problem-solving, working memory, and multi-tasking. Various established tests exist that are designed to evaluate these functions qualitatively or quantitatively, which can be used to demonstrate efficacy.

The selective PDE4 B inhibitor can be administered to the subject or contacted to the brain cells, spinal cord cells, or other neural cells to improve cognitive impairment or improve sensory function, motor function, or paralysis when the cognitive impairment, sensory function, motor function, or paralysis is measurable or has persisted for at least two, at least four, or at least six weeks, or at least 1, 2, 3, 4, 6, or 9 months or at least 1, 2, 3, 4, 5, or more years following a brain injury, and the administration or contacting of the selective PDE4 B inhibitor is initiated or repeated at least two, at least four, or at least six weeks, or at least 1, 2, 3, 4, 6, or 9 months or at least 1, 2, 3, 4, 5, or more years following the brain injury or SCI. In some cases, the cognitive impairment, sensory function, motor function, or paralysis has persisted for at least 1, 2, 3, 4, 5, 6, 8, or 10 years following a brain injury or SCI, and the administration of or contacting of the selective PDE4 B inhibitor is initiated or repeated at least 1, 2, 3, 4, 5, 6, 8, or years following the brain injury or SCI.

The selective PDE4 B inhibitor can be administered orally or intravenously, or intracranially, intracerebrally, intracerebroventricularly, epidurally, or intrathecally. Repeated administration is contemplated at intervals to achieve the benefits described herein, and for as long a period of time as repeated administration has demonstrated benefit. For example, in some variations, the inhibitor or inhibitor composition is administered for at least 2 weeks, at least 4 weeks, at least 6 weeks, at least 2 months, at least four months, or longer. In some variations, administration continues for not more than 6 months or not more than 1 year. The inhibitor or inhibitor composition can be administered in combination with or after rehabilitation therapy. It can be administered in combination with (concurrent) or after a first therapy administered to treat the injury. In some variations, the first therapy is selected from tissue plasminogen activator, urokinase, and progesterone. In some variations, the inhibitor or inhibitor composition is administered as a co-therapy with embroyic stem cells, pluripotent stems cells, or neural precursor cells.

Further contemplated are methods comprising contacting a selective PDE4 B inhibitor to cells (e.g., brain, neural, spinal cells) of a mammalian subject that has suffered a TBI, a SCI, or paralysis to improve (a) cognitive function in the mammalian subject with cognitive impairment and/or (b) motor function, sensory function, or paralysis in the mammalian subject.

The selective PDE4 B inhibitor can be a compound having a structure of formula (I):

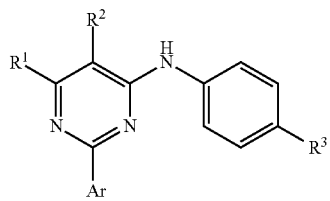

wherein $R^1$ and $R^2$ are each independently $C_1$-$C_4$ alkyl or $C_2$-$C_4$ alkenyl; $R^3$ is $(CH_2)_nCO_2H$; n is 0, 1, or 2; Ar is an optionally substituted aryl or heteroaryl; or a salt, ester, or solvate thereof. In some cases, $R^1$ and $R^2$ are each $C_1$-$C_4$ alkyl. In specific cases, $R^1$ is Me and $R^2$ is Et. In various cases, n is 0. In other cases, n is 1. In various cases, Ar is optionally substituted aryl, and in specific cases Ar is phenyl. In other cases, Ar is optionally substituted thiophenyl, in specific cases 2-thiophenyl or 3-thiophenyl. The Ar can b substituted with one or more of Cl, F, $CH_3$, and $SCH_3$, or can be unsubstituted. In specific cases, the PDE4 B inhibitor is selected from

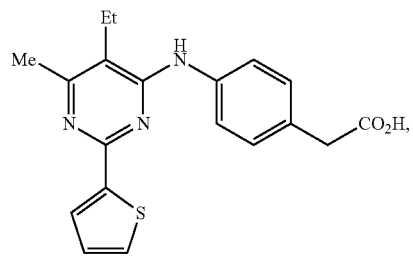

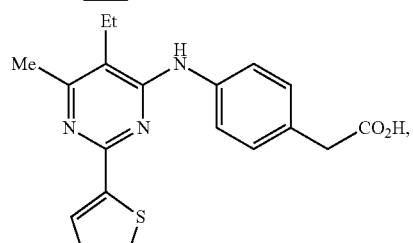

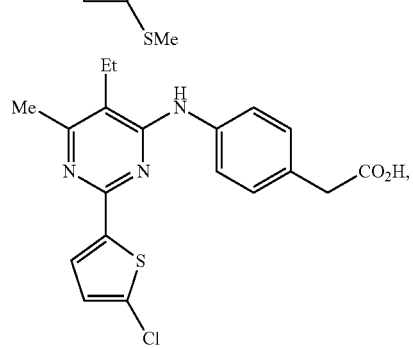

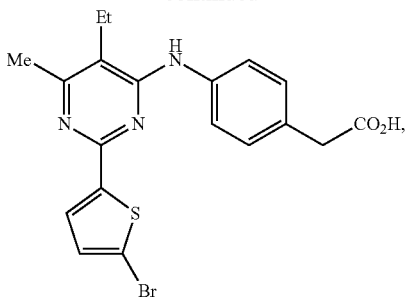 [SMILES: CCc1c(C)nc(-c2ccc(Cl)s2)nc1Nc1ccc(CC(=O)O)cc1]

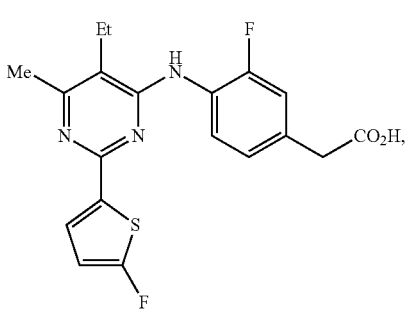

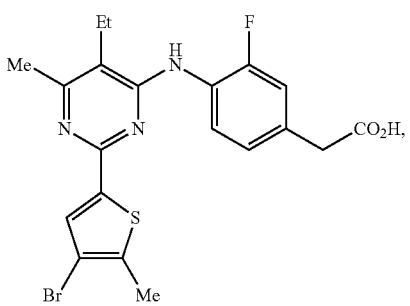

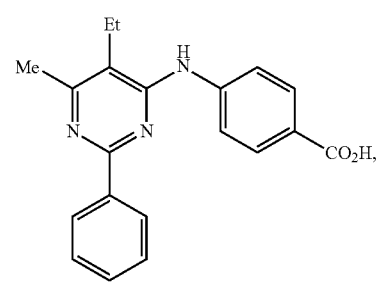

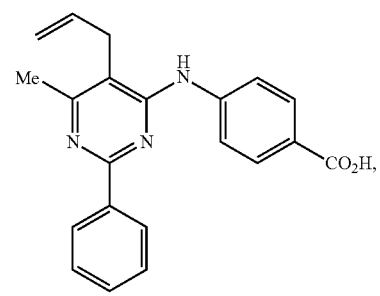

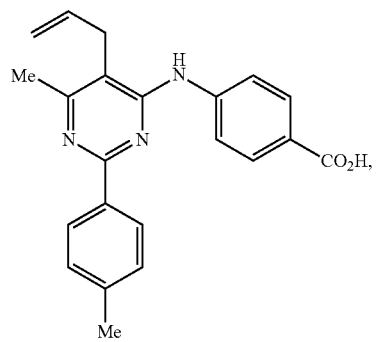
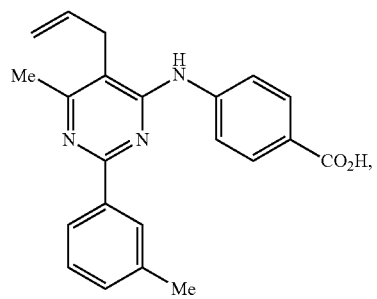
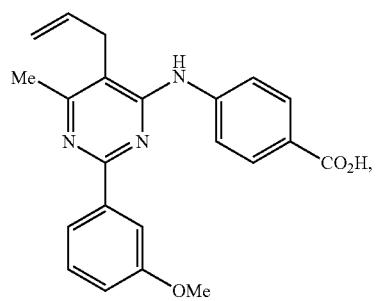
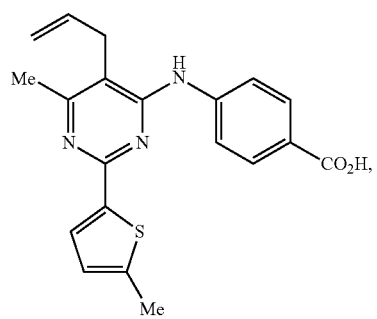
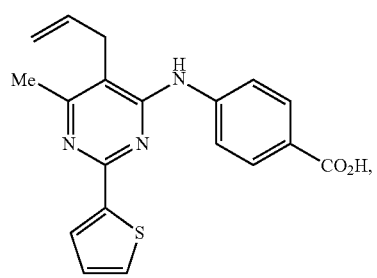
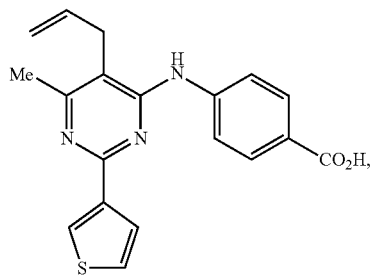
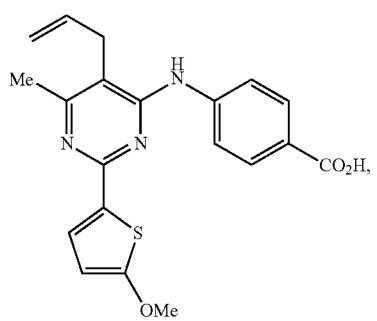
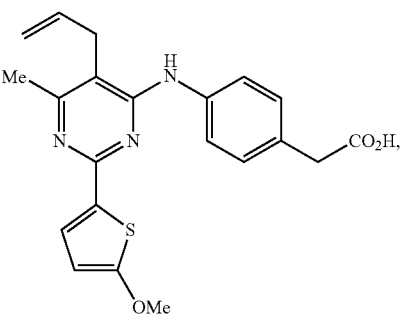
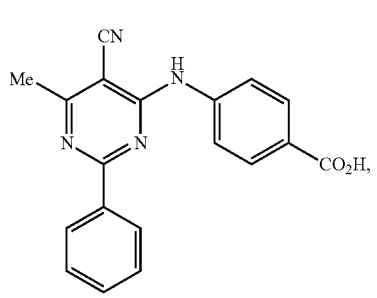
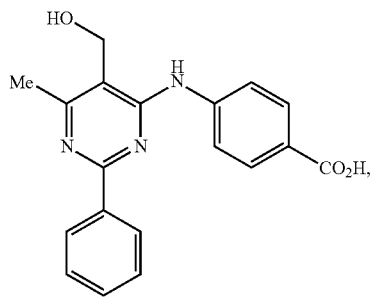
or a salt, ester, or solvate thereof. In some specific cases, the PDE4 B inhibitor is

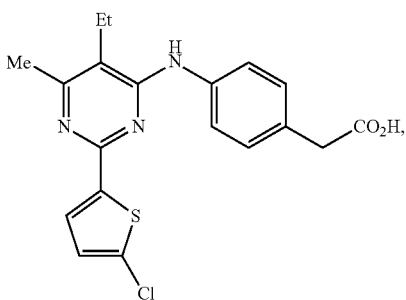 [SMILES: CCc1c(C)nc(-c2ccc(Cl)s2)nc1Nc1ccc(CC(=O)O)cc1]

or a salt, ester or solvate thereof.

For cases wherein the subject suffers a SCI, the methods disclosed herein can further comprise transplanting cells into the spinal cord. In some cases, the cells are stem cells or glial cells, and in specific cases, the cells are Schwann cells.

Additional aspects or variations of the invention include those summarized by the following numbered paragraphs:

1. A method of improving cognitive function in a mammalian subject with cognitive impairment, the method comprising administering to the subject a selective PDE4 B inhibitor, in an amount effective to improve cognitive function.
2. Use of a selective PDE4 B inhibitor to improve cognitive function in a mammalian subject with cognitive impairment.
3. The method or use according to paragraph 1 or 2, wherein the selective PDE4 B inhibitor is formulated in a composition that includes a pharmaceutically acceptable carrier.
4. The method or use according to any one of paragraphs 1-3, wherein the subject is a human.
5. The method or use according to any one of paragraphs 1-4, wherein the cognitive impairment followed a traumatic brain injury.
6. The method or use according to paragraph 5, wherein the traumatic brain injury is a closed traumatic brain injury.
7. The method or use according to paragraph 6, wherein the traumatic brain injury is a penetrating traumatic brain injury.
8. The method or use according to paragraph 6 or 7, wherein the traumatic brain injury results from proximity or exposure to an explosive blast or blast wind.
9. The method or use according to paragraph 5, wherein the traumatic brain injury results from one or more concussion events, or chronic traumatic encephalopathy (CTE).
10. The method or use according to paragraph 9, wherein the one or more concussion events include repeated head trauma from sports or athletics or a vehicular accident.
11. The method or use according to paragraph 5, wherein the traumatic brain injury resulted from a fall or from child or domestic abuse.
12. The method or use according to any one of paragraphs 1-4, wherein the cognitive impairment followed a brain hypoxia event.
13. The method or use according to paragraph 12, wherein the hypoxia event resulted from a cardiac arrest, a myocardial infarction, a stroke, a near suffocation, a near drowning, during general anesthesia, during cardiac surgery, or during open heart surgery.
14. The method or use according to paragraph 13, wherein the hypoxia event occurred prenatally or perinatally.
15. The method or use according to any one of paragraphs 1-14, wherein the improvement to cognitive function comprises improved short term memory.
16. The method or use according to any one of paragraphs 1-15, wherein the improvement to cognitive function comprises improved long term memory.
17. The method or use according to any one of paragraphs 1-16, wherein the improvement to cognitive function comprises improved attention span.
18. The method or use according to any one of paragraphs 1-17, wherein the improvement to cognitive function comprises improved working memory.
19. The method or use according to any one of paragraphs 1-18, wherein the improvement in cognitive function comprises improvement with at least one parameter selected from attention span, judgment, processing speed, distractability, abstract reasoning, planning, problem-solving, working memory, and multi-tasking.
20. The method or use according to any one of paragraphs 5-19, wherein the cognitive impairment is measurable or has persisted past the acute stage of brain injury, and wherein administration of the selective PDE4 B inhibitor is initiated during a subsequent chronic stage following the brain injury.
21. The method or use according to any one of paragraphs 5-19, wherein the cognitive impairment is measurable or has persisted for at least two, at least four, or at least six weeks following a brain injury, and wherein administration of the selective PDE4 B inhibitor is initiated or repeated at least two, at least four, or at least six weeks following the brain injury.
22. The method or use according to any one of paragraphs 6-19, wherein the cognitive impairment is measurable or has persisted for at least two, at least four, or at least six months following a brain injury, and wherein administration of the selective PDE4 B inhibitor is initiated or repeated at least two, at least four, or at least six months following the brain injury.
23. The method or use according to any one of paragraphs 5-19, wherein the cognitive impairment is measurable or has persisted for at least 1, 2, 3, 4, 5, 6, 8, or 10 years following a brain injury, and wherein administration of the selective PDE4 B inhibitor is initiated or repeated at least 1, 2, 3, 4, 5, 6, 8, or 10 years following the brain injury.
24. The method or use according to any one of paragraphs 5-19, wherein the brain injury has been treated with a first therapy selected from tissue plasminogen activator, urokinase, and progesterone, and wherein administration of the selective PDE4B inhibitor is initiated or repeated following cessation of the first therapy.
25. The method or use according to any one of paragraphs 1-24, wherein the selective PDE4 B inhibitor is administered orally or intravenously.
26. The method or use according to any one of paragraphs 1-24, wherein the selective PDE4 B inhibitor is formulated for and/or administered intracranially, intracerebrally, intracerebroventricularly, epidurally, or intrathecally.
27. The method or use according to any one of paragraphs 1-26, wherein the selective PDE4 B inhibitor is administered for at least 2 weeks.
28. The method or use according to any one of paragraphs 1-27, wherein the selective PDE4 B inhibitor is administered for not more than 6 months or 1 year.

29. The method or use according to any one of paragraphs 1-28, wherein the selective PDE4 B inhibitor is administered after or concurrent to rehabilitation therapy.
30. The method or use of any one of paragraphs 1-31, wherein the selective PDE4 B inhibitor has a structure of formula (I):

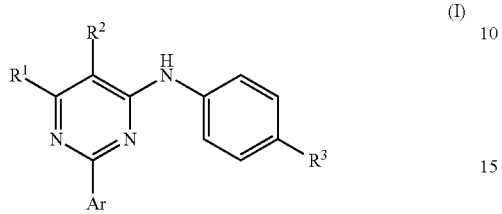

wherein
$R^1$ and $R^2$ are each independently $C_1$-$C_4$ alkyl or $C_2$-$C_4$ alkenyl;
$R^3$ is $(CH_2)_n CO_2 H$;
n is 0, 1, or 2;
Ar is an optionally substituted aryl or heteroaryl;
or a salt, ester, or solvate thereof.

31. The method or use of paragraph 30, wherein $R^1$ and $R^2$ are each $C_1$-$C_4$ alkyl.
32. The method or use of paragraph 31, wherein $R^1$ is Me and $R^2$ is Et.
33. The method or use of any one of paragraphs 30 to 32, wherein n is 0.
34. The method or use of any one of paragraphs 30 to 32, wherein n is 1.
35. The method or use of any one of paragraphs 30 to 34, wherein Ar is optionally substituted aryl.
36. The method or use of paragraph 35, wherein Ar is phenyl.
37. The method or use of any one of paragraphs 30 to 34, wherein Ar is optionally substituted thiophenyl.
38. The method or use of paragraph 37, wherein Ar is optionally substituted 2-thiophenyl.
39. The method or use of paragraph 37, wherein Ar is optionally substituted 3-thiophenyl.
40. The method or use of any one of paragraphs 37 to 39, wherein the thiophenyl is substituted with one or more of Cl, F, $CH_3$, and $SCH_3$.
41. The method or use of any one of paragraphs 37 to 39, wherein the thiophenyl is unsubstituted.
42. The method or use of any one of paragraphs 1-29, wherein the PDE4 B inhibitor is selected from the group consisting of

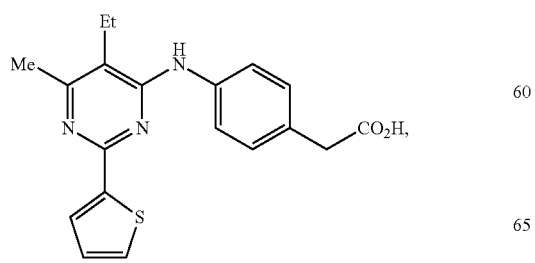

-continued

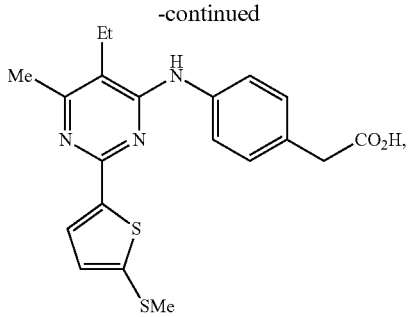

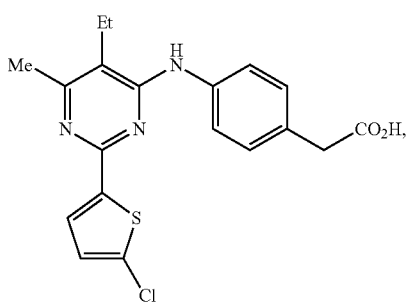 [SMILES: CCc1c(C)nc(-c2ccc(Cl)s2)nc1Nc1ccc(CC(=O)O)cc1]

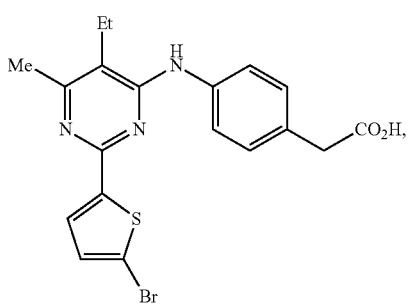

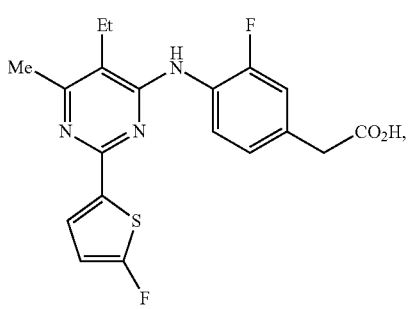

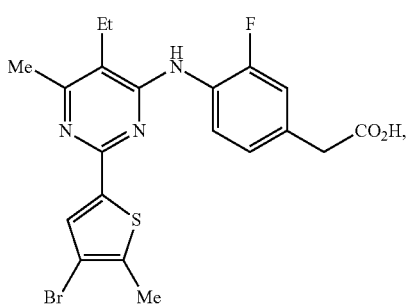

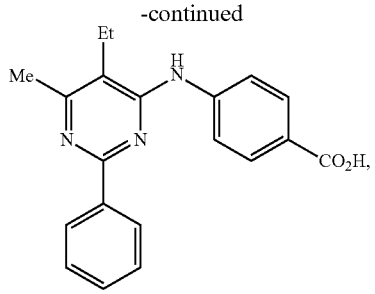
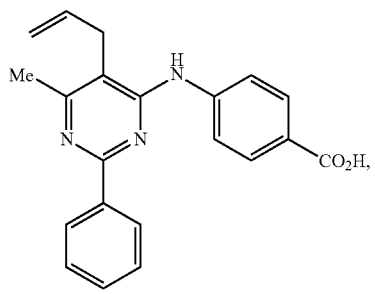
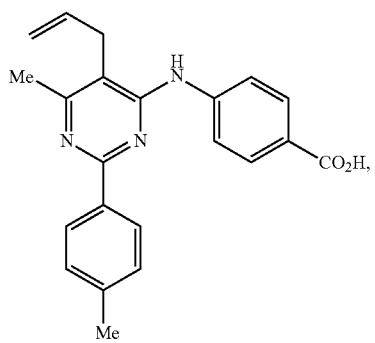
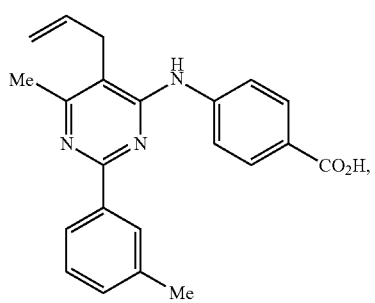
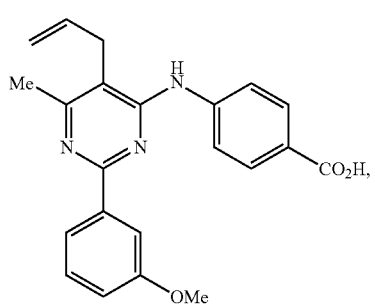
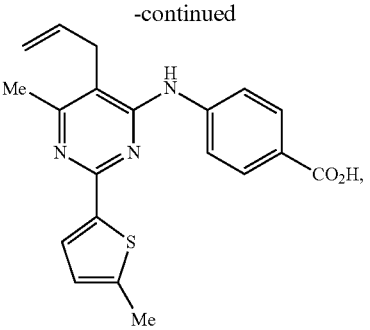
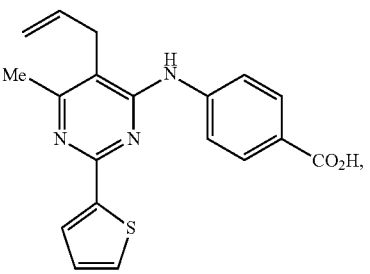
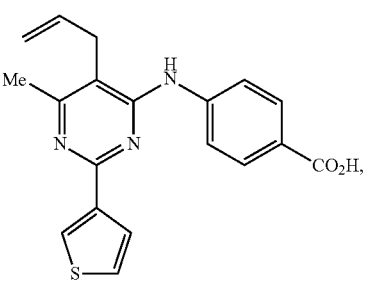
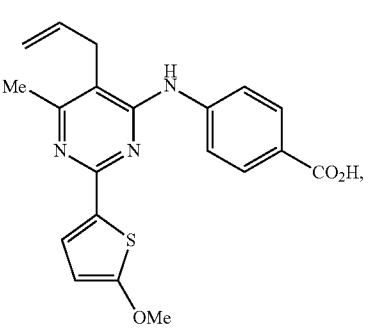
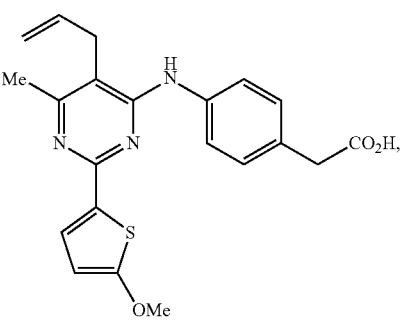

-continued

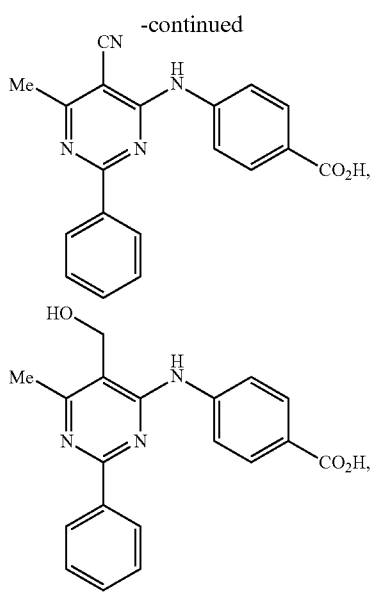

or a salt, ester, or solvate thereof.

43. The method or use of any one of paragraphs 1-29, wherein the selective PDE4 B inhibitor is

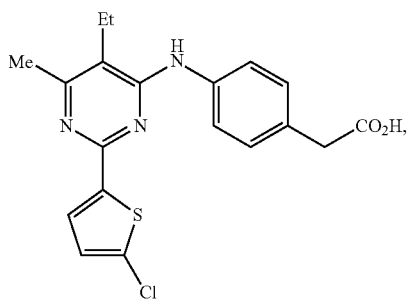

or a salt, ester or solvate thereof.

44. A method of improving one or more of motor function, sensory function and paralysis in a mammalian subject suffering from a spinal cord injury comprising administering to the subject an effective amount of a selective PDE4 B inhibitor to improve one or more of motor function, sensory function and paralysis.

45. Use of a selective PDE4 B inhibitor to improve one or more of motor function, sensory function and paralysis in a mammalian subject suffering from a spinal cord injury.

46. The method or use of paragraph 44 or 45, wherein the selective PDE4 B inhibitor is formulated in a composition that includes a pharmaceutically acceptable carrier.

47. The method or use of any one of paragraphs 44 to 46, wherein the subject is a human.

48. The method or use of any one of paragraphs 44 to 47, further comprising transplanting cells in the spinal cord.

49. The method or use of paragraph 48, wherein the cells are stem cells or glial cells.

50. The method or use of paragraph 49, wherein the cells are Schwann cells.

51. The method or use of any one of paragraphs 44 to 50, wherein the sensory function impairment, motor function impairment, or paralysis is measurable or has persisted for at least two, at least four, or at least six weeks following the spinal cord injury, and wherein administration of the selective PDE4 B inhibitor is initiated at least two, at least four, or at least six weeks following the spinal cord injury.

52. The method or use of any one of paragraphs 44 to 50, wherein the sensory function impairment, motor function impairment, or paralysis is measurable or has persisted for at least two, at least four, or at least six months following the spinal cord injury, and wherein administration of the selective PDE4 B inhibitor is initiated at least two, at least four, or at least six months following the spinal cord injury.

53. The method or use of any one of paragraphs 44 to 50, wherein the sensory function impairment, motor function impairment, or paralysis is measurable or has persisted for at least 1, 2, 3, 4, 5, 6, 8, or 10 years following the spinal cord injury, and wherein administration of the selective PDE4 B inhibitor is initiated at least 1, 2, 3, 4, 5, 6, 8, or 10 years following the spinal cord injury.

54. The method or use of any one of paragraphs 44 to 53, wherein the selective PDE4 B inhibitor has a structure of formula (I):

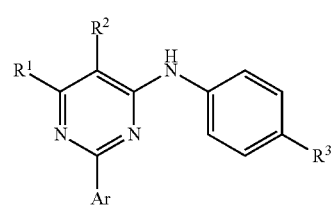

wherein
$R^1$ and $R^2$ are each independently $C_1$-$C_4$ alkyl or $C_2$-$C_4$ alkenyl;
$R^3$ is $(CH_2)_n CO_2 H$;
n is 0, 1, or 2;
Ar is an optionally substituted aryl or heteroaryl;
or a salt, ester, or solvate thereof.

55. The method or use of paragraph 54, wherein $R^1$ and $R^2$ are each $C_1$-$C_4$ alkyl.

56. The method or use of paragraph 55, wherein $R^1$ is Me and $R^2$ is Et.

57. The method or use of any one of paragraphs 54 to 56, wherein n is 0.

58. The method or use of any one of paragraphs 54 to 56, wherein n is 1.

59. The method or use of any one of paragraphs 54 to 58, wherein Ar is optionally substituted aryl.

60. The method or use of paragraph 59, wherein Ar is phenyl.

61. The method or use of any one of paragraphs 54 to 58, wherein Ar is optionally substituted thiophenyl.

62. The method or use of paragraph 61, wherein Ar is optionally substituted 2-thiophenyl.

63. The method or use of paragraph 61, wherein Ar is optionally substituted 3-thiophenyl.

64. The method or use of any one of paragraphs 61 to 63, wherein the thiophenyl is substituted with one or more of Cl, F, $CH_3$, and $SCH_3$.

65. The method or use of any one of paragraphs 61 to 63, wherein the thiophenyl is unsubstituted.

66. The method or use of any one of paragraphs 44 to 53, wherein the PDE4 B inhibitor is selected from the group consisting of
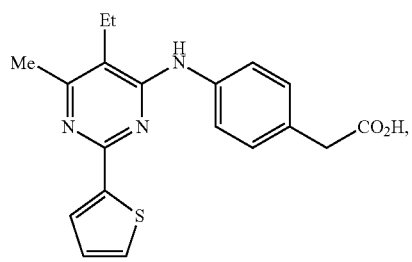
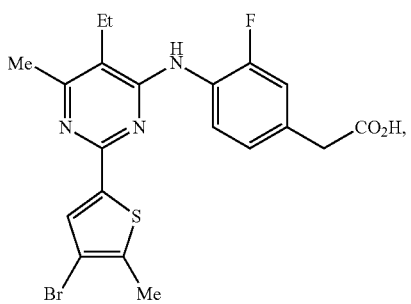
-continued
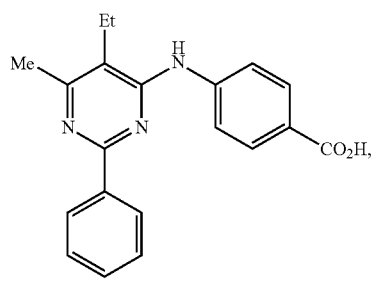
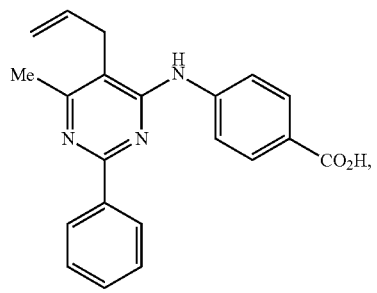
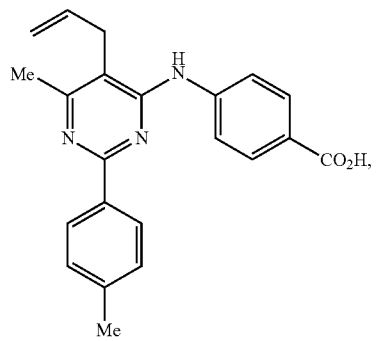
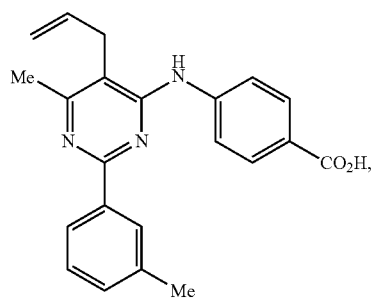

-continued

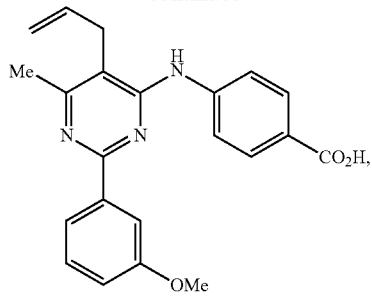

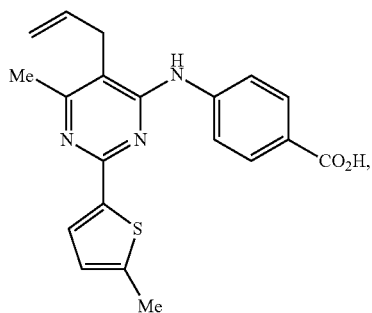

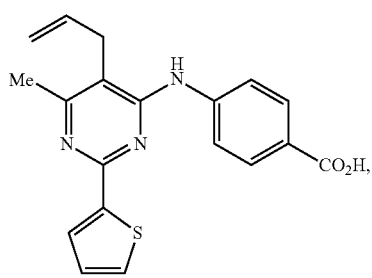

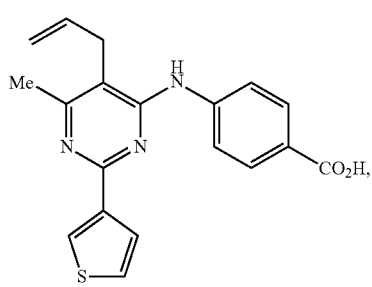

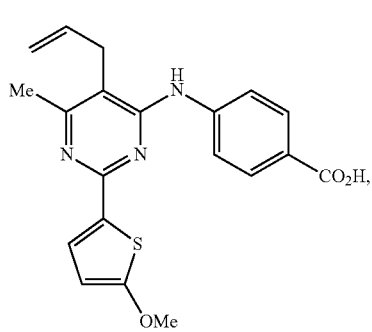

-continued

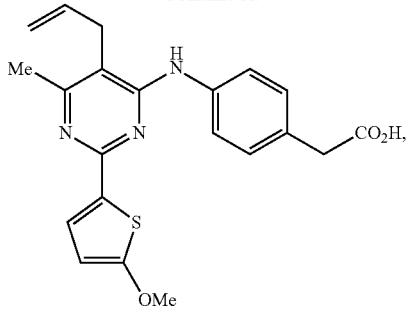

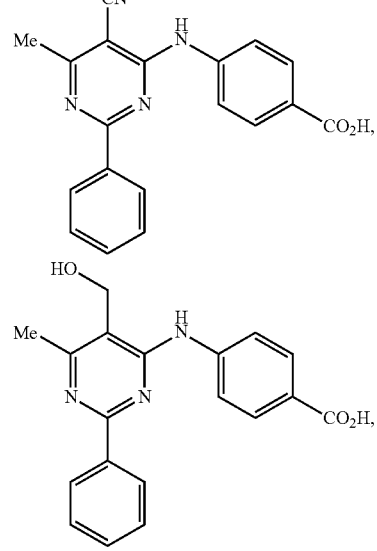

or a salt, ester, or solvate thereof.

67. The method or use of any one of paragraphs 44 to 53, wherein the selective PDE4 B inhibitor is

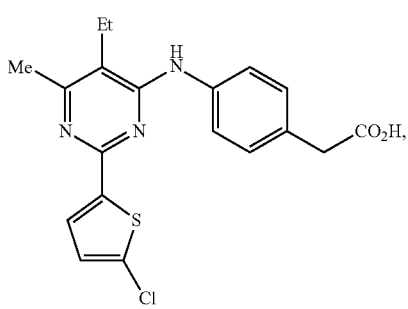

or a salt, ester or solvate thereof.

68. A method of improving cognitive function comprising: examining a human subject who has had a traumatic brain injury to determine if cognitive impairment exists; and
prescribing or administering to a subject identified as having cognitive impairment a composition that comprises a selective PDE4 B inhibitor and a pharmaceutically acceptable diluents, excipient, or carrier.

69. The method of paragraph 68, wherein the examining is performed after treatment for the traumatic brain injury has ceased.

70. The method of paragraph 68 or 69, wherein the examining comprise assessing the subject using the Glasgow Coma Scale or Rancho Los Amigos scale.

71. The method of any one of paragraphs 68-70, wherein the selective PDE4 B inhibitor has a structure of formula (I):

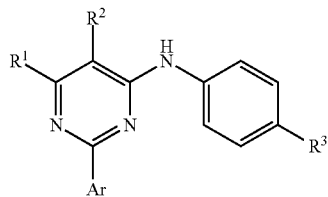

wherein
$R^1$ and $R^2$ are each independently $C_1$-$C_4$ alkyl or $C_2$-$C_4$ alkenyl;
$R^3$ is $(CH_2)_n CO_2H$;
n is 0, 1, or 2;
Ar is an optionally substituted aryl or heteroaryl;
or a salt, ester, or solvate thereof.

The summary is not intended to define every aspect of the invention, and additional aspects are described in other sections, such as the drawing, detailed description, and/or original claims. The entire document is intended to be related as a unified disclosure, and it should be understood that all combinations of features described herein are contemplated, even if the combination of features are not found together in the same sentence, or paragraph, or section of this document. Where the invention as described as a method that involves administration of a compound or composition, it should be understood that equivalent embodiments are contemplated that may be described as the use of the compound or composition for a stated therapeutic indication.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Although the applicant(s) invented the full scope of the invention described herein, the applicants do not intend to claim subject matter described in the prior art work of others. Therefore, in the event that statutory prior art within the scope of a claim 1s brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION

Figure 1:
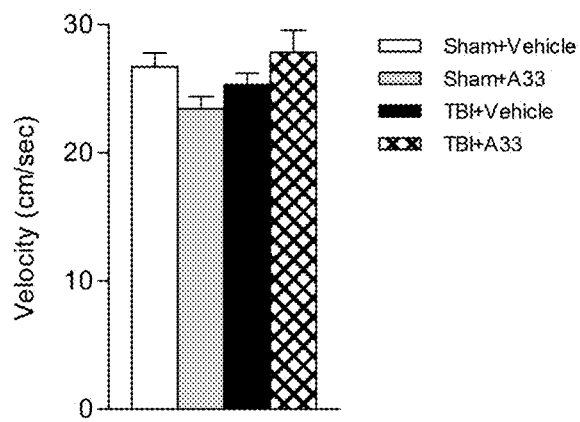
FIG. 1 shows velocity of control (sham) and traumatic brain injury (TBI) rats treated with vehicle compared to compound 33.
Figure 2:
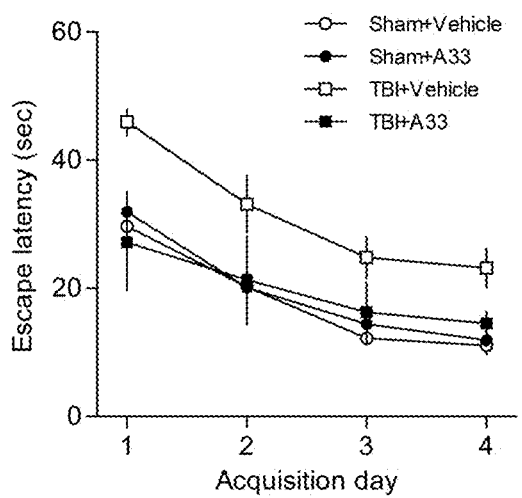
FIG. 2 shows escape latency of control (sham) and traumatic brain injury (TBI) rats treated with vehicle compared to compound 33 over 4 days to monitor improvement in learning ability.
Figure 3:
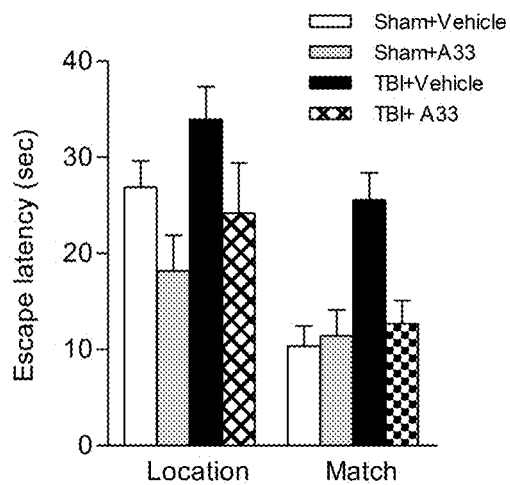
FIG. 3 shows escape latency of control (sham) and traumatic brain injury (TBI) rats treated with vehicle compared to compound 33 for both location and match tasks to monitor working memory ability.
Figure 4:
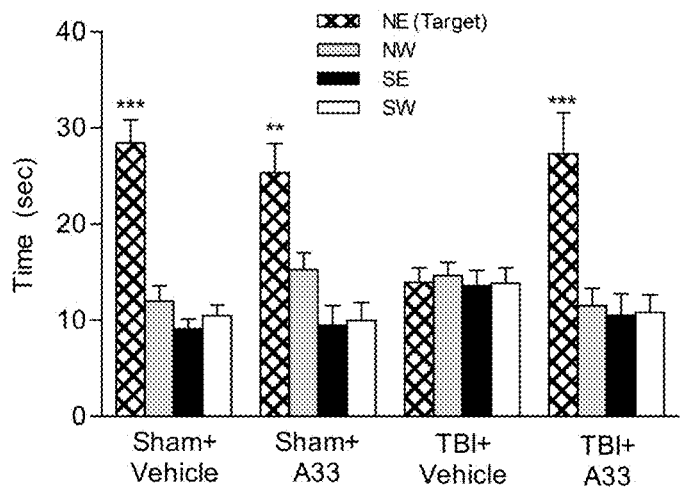
FIG. 4 shows time in various quadrants of a water maze at 24 hours after training to monitor recall ability.

Provided herein are methods of improving cognitive, sensory, or motor function in a subject with cognitive impairment, such as a subject that has suffered a brain injury, or improving sensory function, motor function or paralysis in the TBI patient or a patient that has suffered a spinal cord injury (SCI). These methods comprise administering to a subject a selective PDE4 B inhibitor in an amount effective to improve one or more of cognitive function, sensory function, motor function and paralysis. In a related aspect, provided herein are methods of improving cognitive, sensory, or motor function in a subject with cognitive or motor impairment, such as a subject that has suffered a brain injury by contacting brain cells or other neural cells of the subject with a selective PDE4 B inhibitor in an amount effective to improve one or more of cognitive function, sensory function, and motor function. Further provided are methods of improving sensory function, motor function or paralysis in a TBI patient or a patient that has suffered a SCI or paralysis, by contacting cells (e.g., brain, neural, and/or spinal cells) of the subject with a selective PDE4 B inhibitor in an amount effective to improve one or more of cognitive function, sensory function, motor function and paralysis.

For the methods disclosed herein, the subject is mammalian, and can be human. In various cases disclosed herein, the subject is free of or substantially free of the acute inflammation that may have resulted from the brain injury or SCI.

PDE4 has four different isoforms—A, B, C, and D. Administration of an inhibitor of all four PDE4 isoforms (such as rolipram) has been reported to improve learning and memory in the normal uninjured brains (Blokland, et al., Curr Pharm Des 12(20): 2511-2523 (2006) and Rutten et al., Psychopharmacology (Berl) 196(4): 643-648 (2008))). Moreover, it has been reported that selective PDE4 D inhibitors augment learning and memory in normal uninjured brains (Burgin et al., Nature Biotechnology 28(1): 63-70 (2010)). Studies of PDE4 B gene-deleted mice have reported no augmentation in learning or memory (Siuciak et al., Psychopharmacology (Berl) 197(1): 115-126 (2008)). It has also been reported that inhibition of PDE4 (e.g., with a pan-selective inhibitor such as rolipram) within 30 minutes of a brain injury exacerbates the brain injury, consistent with an effect on vasodilation (Atkins et al., J Neurosci Res 90(9): 1861-1871 (2012)). Additionally, a non-selective PDE4 inhibitor (pentoxyfilline) was reported to have reduced TNF-α (reducing inflammation) and improved outcomes in subjects suffering a brain injury when administered 1 hour after the injury (Shohami et al., J Neuroimmunol 72(2): 169-177 (1997)).

Evidence is presented herein that administration of or contacting brain cells with a selective PDE4 B inhibitor provides improvement to cognitive function in an animal model for cognitive impairment that occurs following a brain injury.

Selective PDE4 B Inhibitors

PDE4 B inhibitors contemplated herein (e.g., for use in compositions, methods, and uses described herein) include compounds as disclosed in US Patent Publication No. 2006/293343, the disclosure of which is incorporated by reference in its entirety. As used herein, the term "selective PDE4 B inhibitor" refers to an inhibitor of PDE4 B that is at least 5 times more selective for inhibiting PDE4 B than one or more of PDE4 A, PDE4 C, and PDE4 D. In some cases, the PDE4 B inhibitor is selective with respect to PDE4 B, compared to each of PDE4 A, C, and D. In various cases, the inhibitor is at least 6 times, at least 7 times, at least 8 times, at least 9 times, at least 10 times, at least 11 times, at least 12 times, at least 13 times, at least 14 times, at least 15 times, at least 20 times, at least 25 times, at least 50 times, at least 100 times, or at least 150 times more selective for inhibiting PDE4 B. An assay for determining selectivity of an inhibitor for PDE4 B and PDE4 D can be found in US Patent Publication No. 2006/293343 and in Naganuma, et al., *Bioorg Med Chem. Lett.*, 19(12): 3174-3176 (2009).

A specifically contemplated class of selective PDE4 B inhibitors are compounds having the formula (I):

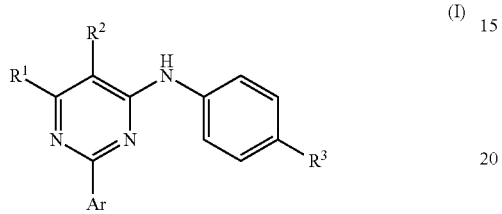

wherein $R^1$ and $R^2$ are each independently $C_1$-$C_4$ alkyl or $C_2$-$C_4$ alkenyl; $R^3$ is $(CH_2)_n CO_2H$; n is 0, 1, or 2; Ar is an optionally substituted aryl or heteroaryl; or a salt, ester, or solvate thereof.

The term "alkyl" used herein refers to a saturated or unsaturated straight or branched chain hydrocarbon group of carbon atoms, including, but not limited to, methyl, ethyl, n-propyl, isopropyl, n-butyl, isobutyl, tert-butyl, and the like. Alkyls of one to four carbon atoms are specifically contemplated.

The term "alkenyl" used herein refers to a straight or branched chain hydrocarbon group of carbon atoms containing at least one carbon double bond including, but not limited to, 1-propenyl, 2-propenyl, 2-methyl-1-propenyl, and the like.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. Particularly contemplated is 2- or 3-thiophenyl.

More specifically, contemplated for use in the methods disclosed herein are selective PDE4 B inhibitors selected from the group of:

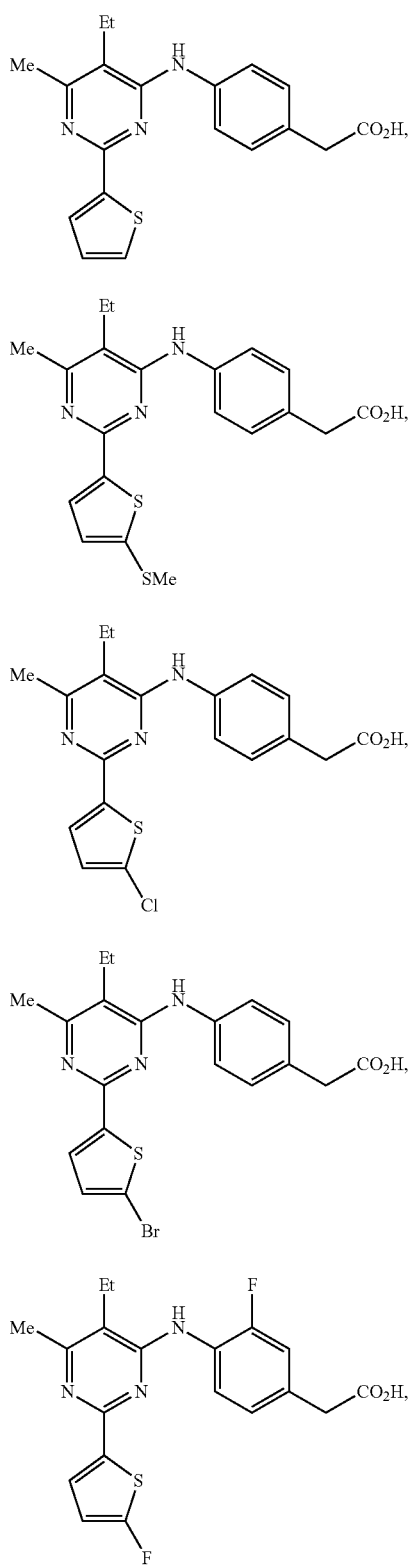

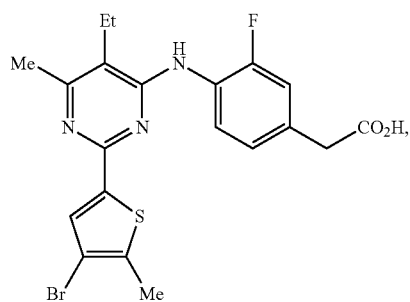
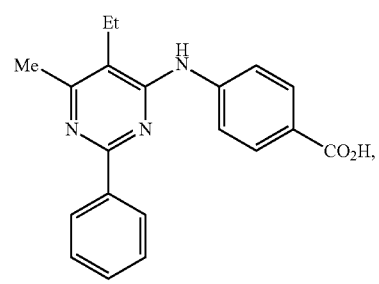
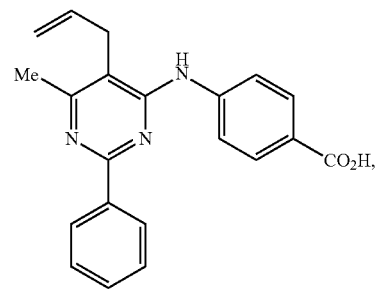
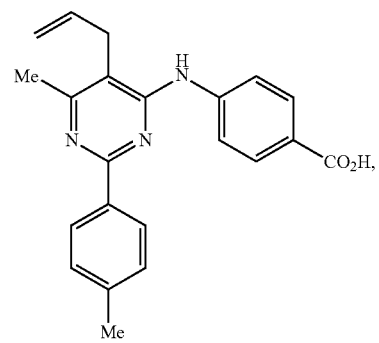
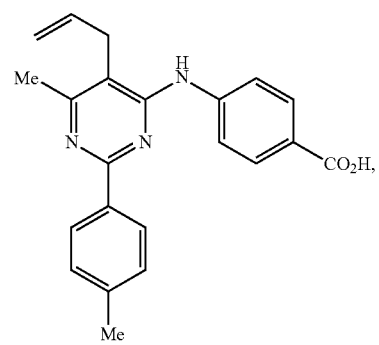
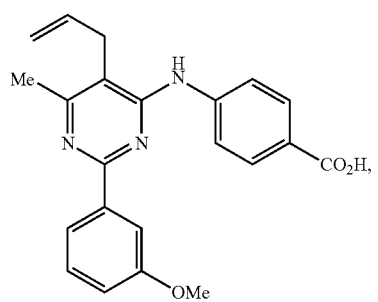
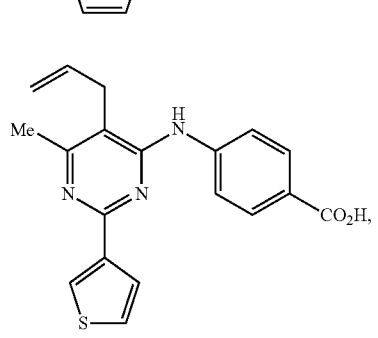
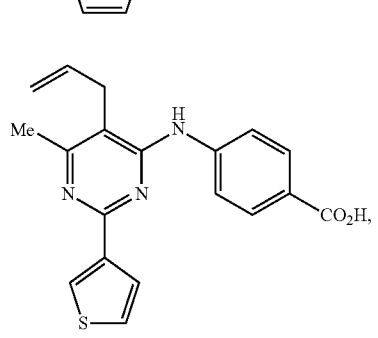
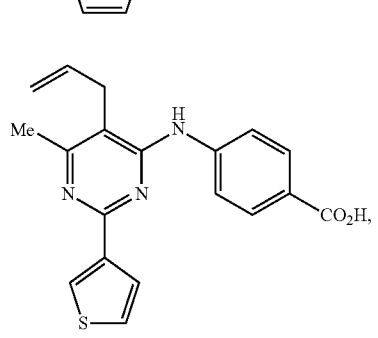
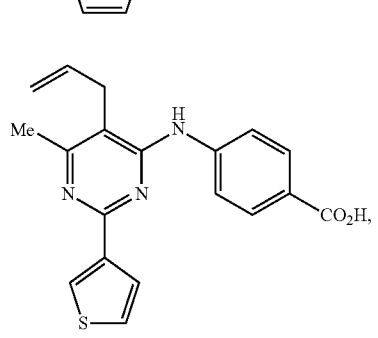

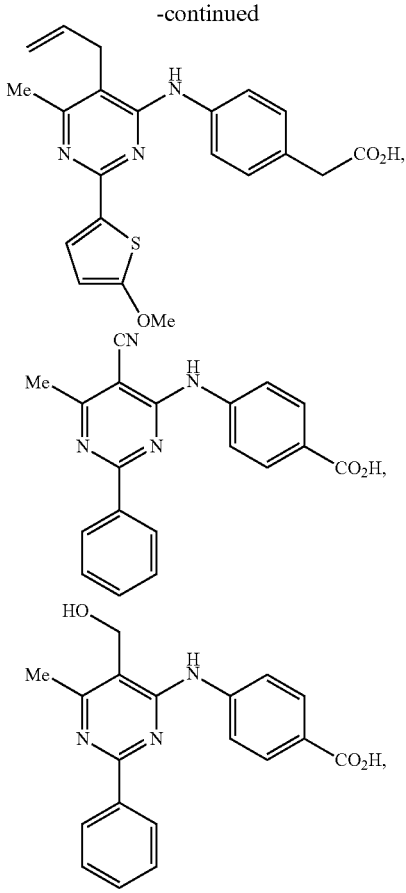

or a salt, ester, or solvate thereof. In various cases, the selective PDE4 B inhibitor is

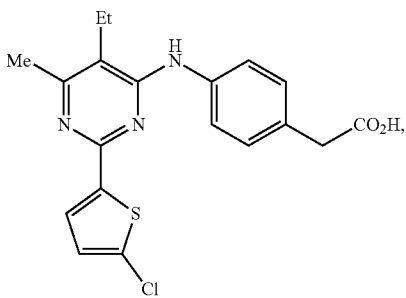 [SMILES: CCc1c(C)nc(-c2ccc(Cl)s2)nc1Nc1ccc(CC(=O)O)cc1]

or a salt, ester or solvate thereof.

The salts, e.g., pharmaceutically acceptable salts, of the disclosed therapeutics may be prepared by reacting the appropriate base or acid with a stoichiometric equivalent of the therapeutic.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Similarly, pharmaceutically acceptable esters and solvates of the therapeutic may be prepared by methods generally known to those skilled in the art. As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The compounds and compositions described herein may also include hydrates and solvates. As used herein, the term "solvate" refers to a complex formed by a solute (herein, the therapeutic) and a solvent. Such solvents for the purpose of the embodiments preferably should not negatively interfere with the biological activity of the solute. Solvents may be, by way of example, water, ethanol, or acetic acid.

Timing of Administration and Duration of Treatment

The methods disclosed herein provide improvement to one or more of cognitive function, motor function, sensory function, and paralysis for the subject that has suffered from a brain injury or SCI. In some variations, the commencement of treatment (administration to the subject of, or contacting of the cells with, the therapeutic) occurs after inflammation due to the injury (e.g., brain injury or spinal cord injury) has substantively diminished. In some variations, the commencement of treatment to improve cognitive function is initiated after treatment of the acute brain injury is completed.

Treatment of cognitive impairment as described herein can be administered or contacted at any time that the impairment is perceptible or measurable, including times long after therapies directed to treatment of an acute brain injury have ceased. In various cases, the cognitive impairment that is treated is measurable or has persisted for at least two, at least four, or at least six weeks following a brain injury or SCI. In some cases, the cognitive impairment that is treated is measurable or has persisted for at least two, at least four, or at least six months following a brain injury or SCI. In various cases, the cognitive impairment that is treated is measurable or has persisted for at least 1, 2, 3, 4, 5, 6, 8, or 10 years following a brain injury or SCI. Also contemplated is treatment of subjects whose cognitive impairment is measurable or has persisted for at least 2 weeks, at least 4 weeks (1 month), at least 2 months, at least 4 months, at least 6 months, at least 9 months, at least 12 months (1 year), at least 18 months, at least 2 years, at least 3 years, at least 4 years, at least 5 years, at least 6 years, at least 7 years, at least 8 years, at least 9 years, or at least 10 years.

In various cases, administration of or contacting of brain or other neural cells with the selective PDE4 B inhibitor is initiated or repeated at least two, at least four, or at least six weeks following the brain injury or SCI. In some cases, administration of or contacting of brain cells or other neural cells with the selective PDE4 B inhibitor is initiated or repeated at least two, at least four, or at least six weeks following the brain injury or SCI. Also contemplated are methods wherein administration of or contacting of brain or other neural cells with the selective PDE4 B inhibitor is initiated or repeated at least 2 weeks, at least 4 weeks (1 month), at least 2 months, at least 4 months, at least 6 months, at least 9 months, at least 12 months (1 year), at least 18 months, at least 2 years, at least 3 years, at least 4 years, at least 5 years, at least 6 years, at least 7 years, at least 8 years, at least 9 years, or at least 10 years following the brain injury of SCI.

Treatment, e.g., repeated or continuous administration of the therapeutic or contacting of cells (e.g., brain, neural, and/or spinal cells) with the therapeutic, can continue for at least a week, at least 2 weeks, at least 3 weeks, at least a month, at least 6 weeks, at least 2 months, at least 3 months, at least 4 months, at least 5 months, at least 6 months, or at least a year. For example, the treatment can be for up to 3 months, up to 4 months, up to 5 months, or up to 6 months. In some cases, the therapeutic is a chronic treatment, e.g., the subject is administered or the cells (e.g., brain, neural, and/or spinal cells) contacted with the therapeutic for at least 1 year, at least 2 years, at least 3 years, at least 4 years, or at least 5 years. In some cases, treatment lasts not more than 6 months or not more than 1 year.

Brain Injury Subjects

Contemplated herein are methods of treating or improving cognitive function in a subject that has suffered a brain injury by administering a selective PDE4 B inhibitor to the subject in an amount effective to improve cognitive function, or contacting cells (e.g., brain and/or neural cells) of a subject that has suffered a brain injury with a selective PDE4 B inhibitor in an amount effective to improve cognitive function. The brain injury can be the result of a traumatic brain injury (TBI) or due to a hypoxia event.

TBI is a nondegenerative, noncongenital insult to the brain from an external mechanical force applied to the cranium and the intracranial contents, possibly leading to permanent or temporary impairment of cognitive, physical, and psychosocial functions, with an associated diminished or altered state of consciousness. TBI can manifest clinically, e.g., as a concussion or coma.

Improvement in cognitive function can be determined by improvement in, or a reduction in the progression of, one or more of the following symptoms: difficulties with attention, difficulties with concentration, distractibility, difficulties with learning, difficulties with short-term or long-term memory, slowness of speed of processing, confusion, perseveration, impulsiveness, difficulties with language processing, difficulties with speech and language, not understanding the spoken word (receptive aphasia), difficulty speaking and being understood (expressive aphasia), slurred speech, speaking very fast or very slow, problems reading, problems writing, difficulties with interpretation of touch, temperature, movement, limb position and fine discrimination, difficulty with the integration or patterning of sensory impressions into psychologically meaningful data, partial or total loss of vision, weakness of eye muscles and double vision (diplopia), blurred vision, problems judging distance, involuntary eye movements (nystagmus), intolerance of light (photophobia), a decrease or loss of hearing, ringing in the ears (tinnitus), increased sensitivity to sounds, loss or diminished sense of smell (anosmia), loss or diminished sense of taste, seizures, convulsions associated with epilepsy, physical paralysis/spasticity, chronic pain, loss of control of bowel and/or bladder, sleep disorders, loss of stamina, appetite changes, dysregulation of body temperature, menstrual difficulties, social-emotional difficulties, dependent behaviors, lack of emotional ability, lack of motivation, irritability, aggression, depression, disinhibition, or lack of awareness. Further contemplated are methods wherein cognitive impairment is improved by improvement of one or more of short term memory, long term memory, attention span, and working memory. Also contemplated is improvement in one or more of attention span, judgment, processing speed, distractability, abstract reasoning, planning, problem-solving, working memory, and multi-tasking.

The methods for treating cognitive impairment provided herein also encompass the treatment of cognitive impairment that has resulted from the TBI injuries that range in scope from mild to severe. A traumatic brain injury can be classified as mild if loss of consciousness and/or confusion and disorientation is shorter than 30 minutes. Thus, in some embodiments, the invention provides for the administration of an effective dose of a selective PDE4 B inhibitor to an individual affected with a TBI or contacting cells (e.g., brain and/or neural cells) of an individual affected with a TBI with an effective dose of a selective PDE4 B inhibitor, wherein said effective dose is an amount of the selective PDE4 B inhibitor sufficient, e.g., to cause a detectable improvement in, reduce the severity of, or reduce the progression of one or more symptoms of mild TBI, including, but not limited to, cognitive problems such as headache, memory problems, attention deficits, mood swings and frustration, fatigue, visual disturbances, memory loss, poor attention/concentration, sleep disturbances, dizziness/loss of balance, irritability, emotional disturbances, feelings of depression, seizures, nausea, loss of smell, sensitivity to light and sounds, mood changes, getting lost or confused, or slowness in thinking.

In some embodiments, the invention provides for the administration of an effective dose of a selective PDE4 B inhibitor to an individual affected with a TBI, or methods of contacting cells (e.g., brain and/or neural cells) of an individual affected with a TBI with an effective dose of a selective PDE4 B inhibitor, wherein said effective dose is an amount of the selective PDE4 B inhibitor sufficient, e.g., to cause a detectable improvement in, reduce the severity of, or reduce the progression of, one or more symptoms of cognitive impairment, including, but not limited to, cognitive deficits such as difficulties with attention, concentration, distractibility, memory, speed of processing, confusion, perseveration, impulsiveness, language processing, speech and language, not understanding the spoken word (receptive aphasia), difficulty speaking and being understood (expressive aphasia), slurred speech, speaking very fast or very slow, problems reading, problems writing; sensory deficits, such as difficulties with interpretation of touch, temperature, movement, limb position or fine discrimination; perceptual deficits, such as difficulty with the integration or patterning of sensory impressions into psychologically meaningful data; visual deficits, including partial or total loss of vision, weakness of eye muscles and double vision (diplopia), blurred vision, problems judging distance, involuntary eye movements (nystagmus), intolerance of light (photophobia); hearing deficits, including a decrease or loss of hearing, or ringing in the ears (tinnitus), or increased sensitivity to sounds; olfactory deficits, including loss or diminished sense of smell (anosmia); loss or diminished sense of taste; seizures, including the convulsions associated with epilepsy that can be several types and can involve disruption in consciousness, sensory perception, or motor movement; physical changes, including physical paralysis/spasticity; chronic pain, loss of control of bowel and bladder, sleep disorders, loss of stamina, appetite changes, dysregulation of body temperature, and menstrual difficulties; social-emotional difficulties, including dependent behaviors, lack of emotional ability, lack of motivation, irritability, aggression, depression, disinhibition, or denial/lack of awareness.

In various embodiments, provided herein are methods for the administration of an effective dose of a selective PDE4 B inhibitor to an individual affected with cognitive impairment following TBI or other brain injury or methods of contacting brain cells of a individual affected with cognitive impairment following TBI or other brain injury with an effective dose of a selective PDE4 B inhibitor, wherein said effective dose is an amount of the selective PDE4 B inhibitor sufficient, e.g., to cause a detectable improvement in, reduce the severity of, or reduce the progression of, one or more symptoms of cognitive impairment listed above. Any established evaluative techniques can be used to demonstrate or detect improvement, including those described herein. The assessment of said improvement or reduction in the progression of one or more symptoms of cognitive impairment can be determined according to the judgment of a practitioner in the art. The assessment of said improvement or reduction in the progression of one or more symptoms of cognitive impairment can be determined according to the judgment of a practitioner in the art in combination with the subjective experience of the subject.

An improvement in one or more symptoms of, or a reduction in the progression of one or more symptoms of, said cognitive impairment can be detected in accordance with the Glasgow Coma Scale (GCS). The GSC provides a scale as follows: (A) Eye Opening Spontaneous=4; To speech=3; To painful stimulation=2; No response=1; (B) Motor Response Follows commands=6; Makes localizing movements to pain=5; Makes withdrawal movements to pain=4; Flexor (decorticate) posturing to pain=3; Extensor (decerebrate) posturing to pain=2; No response=1; (C) Verbal Response Oriented to person, place, and date=5; Converses but is disoriented=4; Says inappropriate words=3; Says incomprehensible sounds=2; No response=1

The severity of TBI according to the GCS score is as follows: Vegetative TBI=less than 3 (characterized by sleep wake cycles; arousal, but no interaction with environment; no localized response to pain); Severe TBI=3-8 (characterized by coma: unconscious state; no meaningful response, no voluntary activities); Moderate TBI=9-12 (characterized by loss of consciousness greater than 30 minutes; physical or cognitive impairments which may or may resolve; patient may benefit from rehabilitation); Mild TBI=13-15 (characterized by a brief change in mental status (confusion, disorientation or loss of memory) or loss of consciousness for less than 30 minutes).

An improvement in one or more symptoms of, or a reduction in the progression of one or more symptoms of, said cognitive impairment can be detected in accordance with the Ranchos Los Amigos scale. The Ranchos Los Amigos Scale measures the levels of awareness, cognition, behavior and interaction with the environment, according to the following scale: Level I: No Response; Level II: Generalized Response; Level III: Localized Response; Level IV: Confused-agitated; Level V: Confused-inappropriate; Level VI: Confused-appropriate; Level VII: Automatic-appropriate; Level VIII: Purposeful-appropriate.

In various cases, the therapeutically effective amount of the selective PDE4 B inhibitor is an amount sufficient to cause a one, two, three, four, five, six or seven level increase in the score of the patient according to the Rancho Los Amigos Scale. In some embodiments, the therapeutically effective amount of the selective PDE4 B inhibitor is an amount sufficient to raise the subject's awareness, cognition, behavior and interaction with the environment from a level of no response to a level of generalized response, localized response, confused agitation, confused inappropriate response, confused appropriate response, automatic appropriate response or purposeful appropriate response. In some embodiments, the therapeutically effective amount of the selective PDE4 B inhibitor is an amount sufficient to raise the subject's awareness, cognition, behavior and interaction with the environment from a level of generalized response to a level of localized response, confused agitation, confused inappropriate response, confused appropriate response, automatic appropriate response or purposeful appropriate response. In some embodiments, the therapeutically effective amount of the selective PDE4 B inhibitor is an amount sufficient to raise the subject's awareness, cognition, behavior and interaction with the environment from a level of localized response to a level of confused agitation, confused inappropriate response, confused appropriate response, automatic appropriate response or purposeful appropriate response. In some embodiments, the therapeutically effective amount of the selective PDE4 B inhibitor is an amount sufficient to raise the subject's awareness, cognition, behavior and interaction with the environment from a level of confused agitation to a level of confused inappropriate response, confused appropriate response, automatic appropriate response or purposeful appropriate response. In some embodiments, the therapeutically effective amount of the selective PDE4 B inhibitor is an amount sufficient to raise the subject's awareness, cognition, behavior and interaction with the environment from a level of confused inappropriate response to a level of confused appropriate response, automatic appropriate response or purposeful appropriate response. In some embodiments, the therapeutically effective amount of the selective PDE4 B inhibitor is an amount sufficient to raise the subject's awareness, cognition, behavior and interaction with the environment from a level of confused appropriate response to a level of automatic appropriate response or purposeful appropriate response. In some embodiments, the therapeutically effective amount of the selective PDE4 B inhibitor is an amount sufficient to raise the subject's awareness, cognition, behavior and interaction with the environment from a level of automatic appropriate response to a level of purposeful appropriate response.

In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test; or the explicit 3-alternative forced choice task. See Folstein et al., J Psychiatric Res 12: 189-98, (1975); Robbins et al., Dementia 5: 266-81, (1994); Rey, L'examen clinique en psychologie, (1964); Kluger et al., J Geriatr Psychiatry Neurol 12:168-79, (1999); Marquis et al., 2002 and Masur et al., 1994.

In animal model systems, cognitive function may be measured in various conventional ways known in the art, including using a Morris Water Maze (MWM), Barnes circular maze, elevated radial arm maze, T maze or any other mazes in which the animals use spatial information. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

Cognitive function can be measured using one or more of the following tests: Brief Symptom Inventory; Rivermead Post Concussive Symptom Questionnaire; Brief Test of Head Injury; Boston Naming Test; Wechsler Memory Scale-IV; Functional Independence Measure; Trail Making Test; Wisconsin Card Sorting Test; or Wechsler Adult Intelligence Scale Working Memory Index.

Also contemplated herein are methods of treating a subject having cognitive impairment that resulted from a brain injury due to a hypoxia event. Hypoxia events include those which result from reduced oxygenation of the brain. Cognitive impairment resulting from an event which reduces the availability of oxygen to the brain, resulting in stress, damage, and finally, cell death, can be improved using a selective PDE4 B inhibitor as disclosed herein. Hypoxia events can arise from or include, but are not limited to, stroke, vascular occlusion, prenatal or postnatal oxygen deprivation, near suffocation, choking, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmia, nitrogen narcosis, hypoxemic hypoxia (altitude sickness, high altitude pulmonary edema, high altitude cerebral edema, sleep apnea, hypopnea, respiratory arrest, shunts), methaemoglobinaemia, histotoxic hypoxia, intrauterine hypoxia, and deficits caused by open heart surgery, cardiac surgery, general anesthesia, or heart-lung bypass procedures. Further contemplated are treatment of cognitive impairment following brain injuries resulting from a cardiac arrest, a myocardial infarction, a stroke, a near suffocation, a near drowning, during general anesthesia, during cardiac surgery, or during open heart surgery.

Spinal Cord Injury Subjects

Spinal cord injury is an insult to the spinal cord resulting in a change, either temporary or permanent, in its normal motor, sensory, or autonomic function. SCI includes conditions known as tetraplegia (formerly known as quadriplegia) and paraplegia. Thus, in some embodiments, the individual having, or experiencing, a symptom of or a condition or syndrome related to, a spinal cord injury is tetraplegic or paraplegic.

Tetraplegia refers to injury to the spinal cord in the cervical region, characterized by impairment or loss of motor and/or sensory function in the cervical segments of the spinal cord due to damage of neural elements within the spinal canal. Tetraplegia results in impairment of function in the arms as well as in the trunk, legs and pelvic organs. It does not include brachial plexus lesions or injury to peripheral nerves outside the neural canal.

Paraplegia refers to impairment or loss of motor and/or sensory function in the thoracic, lumbar or sacral (but not cervical) segments of the spinal cord, secondary to damage of neural elements within the spinal canal. With paraplegia, arm functioning is spared, but, depending on the level of injury, the trunk, legs and pelvic organs may be involved. The term is used in referring to cauda equina and conus medullaris injuries, but not to lumbosacral plexus lesions or injury to peripheral nerves outside the neural canal.

Common causes of SCI include, but are not limited to, motor vehicle accidents, falls, violence, sports injuries, vascular disorders, tumors, infectious conditions, spondylosis, Iatrogenic injuries (especially after spinal injections and epidural catheter placement), vertebral fractures secondary to osteoporosis, and developmental disorders.

In certain embodiments, the spinal cord injury can result from, e.g., blunt force trauma, compression, displacement, or the like. In certain embodiments, the spinal cord is completely severed. In certain other embodiments, the spinal cord is damaged, e.g., partially severed, but not completely severed. In other embodiments, the spinal cord is compressed, e.g., through damage to the bony structure of the spinal column, displacement of one or more vertebrae relative to other vertebrae, inflammation or swelling of adjacent tissues, or the like.

The spinal cord injury can be at one or more of the cervical vertebrae. The spinal cord injury can be at one or more of the thoracic vertebrae. The spinal cord injury can be at one or more of the lumbar vertebrae. The spinal cord injury can be at one or more of the sacral vertebrae. In various embodiments, the spinal cord injury is at vertebra C1, C2, C3, C4, C5, C6 or C7; or at vertebra T1, T2, T3, T4, T5, T6, T7, T8, T9, T10, T11 or T12; or at vertebra L1, L2, L3, L4 or L5. In certain other embodiments, the spinal cord injury is to a spinal root exiting the spinal column between C1 and C2; between C2 and C3; Between C3 and C4; between C4 and C5; between C5 and C6; between C6 and C7; between C7 and T1; between T1 and T2; between T2 and T3; between T3 and T4; between T4 and T5; between T5 and T6; between T6 and T7; between T7 and T8; between T8 and T9; between T9 and T10; between T10 and T11; between T11 and T12; between T12 and L1; between L1 and L2; between L2 and L3; between L3 and L4; or between L4 and L5. In certain embodiments, the injury is to the cervical cord. In other embodiments, the injury is to the thoracic cord. In other embodiments the spinal cord injury is to the lumbrosacral cord. In certain other embodiments, the spinal cord injury is to the conus. In certain other embodiments, the CNS injury is to one or more nerves in the cauda equina. In another embodiment, the spinal cord injury is at the occiput.

In various embodiments, a symptom of a spinal cord injury is numbness in one or more dermatomes (i.e., a patch of skin innervated by a given spinal cord level). In specific embodiments, the symptom of a spinal cord injury is numbness in one or more of dermatomes C1, C2, C3, C4, C5, C6, C7, T1, T2, T3, T4, T5, T6, T7, T8, T9, T10, T11, T12, L1, L2, L3, L4 or L5.

The methods disclosed herein provide improvement in sensory function impairment, motor function impairment, or paralysis via administration to the subject of a selective PDE4 B inhibitor or contacting cells (e.g., spinal and/or neural cells) of the subject with a selective PDE4 B inhibitor. The particular technique(s) for detecting an improvement in, a reduction in the severity of, or a reduction in the progression of, one or more symptoms, conditions, or syndromes of SCI is not critical to the method of treating SCI provided herein. In certain embodiments, the assessment of said improvement or reduction in the progression of one or more symptoms, conditions, or syndromes of SCI is determined according to the judgment of the practitioner in the art. In certain embodiments, the assessment of said improvement or reduction in the progression of one or more symptoms, conditions, or syndromes of SCI is determined according to the judgment of the practitioner in the art in combination with the subjective experience of the subject. In some embodiments, an improvement in one or more symptoms of, or a reduction in the progression of one or more symptoms of, said spinal cord injury is detected in accordance with the *International Standards for Neurological and Functional Classification of Spinal Cord Injury*. The *International Standards for Neurological and Functional Classification of Spinal Cord Injury*, published by the American Spinal Injury Association (ASIA), is a widely accepted system describing the level and extent of spinal cord injury based on a systematic motor and sensory examination of neurologic function. See International Standards For Neurological Classification Of Spinal Cord Injury, *J Spinal Cord Med.* 26 Suppl 1:S50-6 (2003), the disclosure of which is hereby incorporated by reference in its entirety.

An improvement in one or more symptoms of, or a reduction in the progression of one or more symptoms of, said spinal cord injury can be detected in accordance with the ASIA Impairment Scale (modified from the Frankel classification), using the following categories: A—Complete: No sensory or motor function is preserved in sacral segments S4-S5.4. "Complete" refers to the absence of sensory and motor functions in the lowest sacral segments. B—Incomplete: Sensory, but not motor, function is preserved below the neurologic level and extends through sacral segments S4-S5. "Incomplete" refers to preservation of sensory or motor function below the level of injury, including the lowest sacral segments. C—Incomplete: Motor function is preserved below the neurologic level, and most key muscles below the neurologic level have muscle grade less than 3. D—Incomplete: Motor function is preserved below the neurologic level, and most key muscles below the neurologic level have muscle grade greater than or equal to 3. E—Normal: Sensory and motor functions are normal.

An improvement in one or more symptoms of, or a reduction in the progression of one or more symptoms of said spinal cord injury can be detected by measuring the muscle strength of the patient. In some embodiments, muscle strength can be graded using the following Medical Research Council (MRC) scale of 0-5: 5—Normal power; 4+—Submaximal movement against resistance; 4—Moderate movement against resistance; 4⁻—Slight movement against resistance; 3—Movement against gravity but not against resistance; 2—Movement with gravity eliminated; 1—Flicker of movement; 0—No movement.

Dosing and Formulations of PDE4 B Inhibitors

The terms "therapeutically effective amount" and "prophylactically effective amount," as used herein, refer to an amount of a compound sufficient to treat, ameliorate, or prevent the identified condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration or contacting. Therapeutically and prophylactically effective amounts for a given situation can be determined by routine experimentation that is within the skill and judgment of the clinician.

The term "contacting cells" refers to human intervention with a therapeutic to create interaction between the target cells (e.g., brain, neural, and/or spinal cells) and the compound of interest. In some cases, the compound administered to the subject with the TBI, SCI or paralysis is the same compound that contacts the cells (or a composition that comprises the compound in a therapeutic formulation). In other cases, the compound that contacts the cells is formed in vivo, e.g., a prodrug compound is administered to the subject and metabolized in the subject into the compound, which contacts the cells of interest (e.g., brain, neural, and/or spinal cells) in vivo. In cell therapy variations, appropriate neural or neural precursor cells can be directly contacted ex vivo with the compound prior to introducing the cells into the subject.

The term "prescribing" in the context of the invention refers to indirectly administering to a subject by providing an order such as an instruction to another medical practitioner, or providing a prescription to be filled by a pharmacist or other medical dispensary, or similar instruction such that the subject is administered the therapeutic agent by another medical practitioner or self-administers the therapeutic agent provided by the pharmacist/dispensary, in a therapeutically effective amount.

Dosages of the therapeutic can be administered to a subject or contacted to cells as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg. The therapeutic can be administered or contacted once a day, twice a day, three times a day, every other day, twice a week, once a week, once every two weeks or once a month.

As herein, the compounds described herein may be formulated in pharmaceutical compositions with a pharmaceutically acceptable excipient, carrier, or diluent. The compound or composition comprising the compound is administered by any route that permits treatment of the condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intracranially, intracerebrally, intracerebroventricularly, epidurally, intrathecally, topically, transdermally, rectally, orally, nasally or by inhalation. In some variations, the route of delivery is oral and the compound or composition is formulated as a pill or capsule. In some cases, the route of delivery is intra-nasal. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration of a compound directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical compound into the cerebrospinal fluid ("spinal injection") is known in the art, and is suited for administration of the present compounds. Use of protein transduction domains and other peptides and non-peptide moieties known in the art may also be used to facilitate transport across the blood-brain barrier.

Pharmacologic-based procedures are also known in the art for circumventing the blood brain barrier, including the conversion of hydrophilic compounds into lipid-soluble drugs. The active agent can be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with compounds to be delivered to the interstitial fluid compartment of the brain, to cause an increase in the permeability of the blood-brain barrier and effect increased delivery of the compounds to the brain.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. Examples of suitable carriers include pyridinium, fatty acids, inositol, cholesterol, and glucose derivatives also add vitamin C. The carrier can be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 to Pardridge et al. These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198 to Poduslo et al. Specific carrier molecules disclosed include hemoglobin, lysozyme, cytochrome c, ceruloplasmin, calmodulin, ubiquitin and substance P. See also U.S. Pat. No. 5,017,566 to Bodor.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the condition.

In an embodiment, the pharmaceutical compositions are formulated with one or more pharmaceutically acceptable excipients, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents.

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Combination Therapy

Also provided herein are methods for the treatment of an individual having, or experiencing, cognitive impairment due to a brain injury, comprising administering to the individual a selective PDE4 B inhibitor as disclosed herein in an amount sufficient to cause a detectable improvement in cognitive impairment, or a reduction in the progression of cognitive impairment, and one or more therapeutic agents. For example, the selective PDE4 B inhibitor can be administered in conjunction with seizure prevention medications. Seizure prevention medications may be given early in the course of treatment and later if the individual has seizures. In some embodiments, medications to control spasticity may be used as the patient recovers function. In addition, medications may be used to improve attention and concentration (e.g., amantadine and methylphenidate, bromocriptine and antidepressants), or to control aggressive behavior (e.g., carbamamazapine and amitriptyline). Additionally contemplated is concurrent rehabilitative therapy.

Stem Cell Transplantation and Use of PDE4 B Inhibitors

Further provided herein are methods for the treatment of an individual having, or experiencing, a symptom of SCI, comprising administering to the individual a selective PDE4 B inhibitor as disclosed herein in an amount sufficient to cause a detectable improvement in one or more symptoms, or a reduction in the progression of one or more symptoms of, said SCI, in combination with transplanting stem cells or neural progenitor cells. Also provided are methods for the treatment of an individual having, or experiencing, a symptom of SCI, comprising contacting spinal or neural cells of the individual with a selective PDE4 B inhibitor as disclosed herein in an amount sufficient to cause a detectable improvement in one or more symptoms, or a reduction in the progression of one or more symptoms of, said SCI, in combination with transplanting stem cells or neural progenitor cells. For example, the selective PDE4 B inhibitor can be administered in conjunction with transplantation into the spinal cord of cells, or the selective PDE4 B inhibitor can be contacted in conjunction with transplantation into the spinal cord of cells. Contemplated cells include stem cells (e.g., pluripotent or embryonic stem cells), neural progenitor cells, and glial (e.g., Schwann) cells.

Stem cells are cells with the ability to divide for indefinite periods in culture to give rise to specialized cells. The term "somatic stem cell" or "adult stem cell" refers to undifferentiated cells, found among differentiated cells within a tissue or organ, which has the capacity for self-renewal and differentiation. The somatic stem cells can differentiate to yield some or all of the major specialized cell types of the renewable tissue or organ. The primary role of somatic stem cells is to maintain and repair the tissue in which they are found.

Somatic stem cells can be used for transplantation. For example, the invention provides for methods of transplanting somatic stem cells to treat an SCI or to reduce the damage to the spinal cord in a patient suffering from an SCI. Exemplary somatic stem cells include hematopoietic stem cells, mesenchymal stem cells, neural stem cells, endothelial stem cells, and neural crest stem cells.

Mesenchymal Stem Cells: "Mesenchymal stem cells" (MSC) are non-hematopoietic, pluripotent, self-renewing progenitor cells with a characteristic spindle-shaped morphology. These cells are derived from immature embryonic connective tissue (mesoderm layer).

MSC have been shown to contribute to the maintenance and regeneration of various connective tissues. (Pittenger et al., Science 1999; 284(5411):143-7) MSC differentiate into a number of cell types, including chondrocytes, bone, fat, cells that support the formation of blood, and fibrous connective tissue.

MSC are mobilized from bone marrow in response to tissue injury to aid in repair after a variety of end organ injury-models including models of myocardial infarction (Kawada et al., Blood 2004; 104:3581-7), spinal cord injury (Koda et al., Neuroreport 2005; 16:1763-7), renal ischemia/reperfusion injury (Togel et al., Am J Physiol Renal Physiol 2005; 289:F31-42) and intestinal radiation injury (Zhang et al., J Biomed Sci 2008; 15:585-94).

Mesenchymal stem cells may be isolated from various tissues including but not limited to bone marrow (denoted as BM-MSC herein), peripheral blood, blood, placenta, and adipose tissue and amniotic fluid (denoted as AF-MCS herein) Exemplary methods of isolating mesenchymal stem cells from bone marrow are described in (Phinney et al., J Cell Biochem 1999; 72(4):570-85), from amniotic fluid (Baghaban et al., Arch Iran Med 2011; 14(2):96-103), from peripheral blood are described by Kassis et al. (Bone Marrow Transplant. 2006 May; 37(10):967-76), from placental tissue are described by Zhang et al. (Chinese Medical Journal, 2004, 117 (6):882-887), from adipose tissue, placental and cord blood mesenchymal stem cells are described by Kern et al. (Stem Cells, 2006; 24:1294-1301).

The mesenchymal stem cells may be characterized using structural phenotypes. For example, the cells used herein can show a morphology similar to that of mesenchymal stem cells (a spindle-like morphology). Alternatively or additionally, the MSC may be characterized by the expression of one or more surface markers. Exemplary MSC surface markers include but are not limited to CD105+, CD29+, CD44+, CD90+, CD73+, CD105+, CD166+, CD49+, SH(1), SH(2), SH(3), SH(4), CD14−, CD34−, CD45−, CD19−, CD5−, CD20−, CD11B−, FMC7− and HLA class 1 negative. Other mesenchymal stem cell markers include but are not limited to tyrosine hydroxylase, nestin and H—NF.

Examples of cells derived from mesenchymal cells include (1) cells of the cardiovascular system such as endothelial cells or cardiac muscle cells or the precursor cells of the cells of the cardiovascular system, and cells having the properties of these cells; (2) cells of any one of bone, cartilage, tendon and skeletal muscle, the precursor cells of the cells of any one of bone, cartilage, tendon, skeletal muscle and adipose tissue, and the cells having the properties of these cells; (3) neural cells or the precursor cells of neural cells, and the cells having the properties of these cells; (4) endocrine cells or the precursor cells of endocrine cells, and the cells having the properties of these cells; (5) hematopoietic cells or the precursor cells of hematopoietic cells, and the cells having the properties of these cells; and (6) hepatocytes or the precursor cells of hepatocytes, and the cells having the properties of these cells.

Methods of mesenchymal cell culture are well known in the art of cell culturing (see, for example, Friedenstein et al., Exp Hematol 1976 4, 267-74; Dexter et al. J Cell Physiol 1977, 91:335-44; and Greenberger, Nature 1978 275, 7524). For example, mesenchymal cells are derived from a source selected from the group consisting of endothelial cells, cardiac muscle cells, bone cells, cartilage cells, tendon cells, skeletal muscle cells, bone cells, cartilage cells, tendon cells, adipose tissue cells, neural cells, endocrine cells, hematopoietic cells, hematopoietic precursor cells, bone marrow cells, and the precursor cells thereof, hepatocytes, and hepatocyte precursor cells.

The marrow or isolated mesenchymal stem cells can be autologous, allogeneic or from xenogeneic sources, and can be embryonic or from post-natal sources. Bone marrow cells may be obtained from iliac crest, femora, tibiae, spine, rib or other medullary spaces. Other sources of human mesenchymal stem cells include embryonic yolk sac, placenta, umbilical cord, periosteum, fetal and adolescent skin, and peripheral, circulating blood.

Embryonic Stem Cells: Embryonic stem cells (ESC) are derived from embryos that were developed from eggs that have been fertilized using in vitro fertilization. Procedures for isolating and growing human primordial stem cells are described in U.S. Pat. No. 6,090,622. Human embryonic stem cells (hESCs) can be isolated from human blastocysts obtained from human in vivo preimplantation embryos, in vitro fertilized embryos, or one-cell human embryos expanded to the blastocyst stage (Bongso et al., Hum. Reprod. 4:706, 1989). Human embryos can be cultured to the blastocyst stage in G1.2 and G2.2 medium (Gardner et al., Fertil. Steril. 69:84, 1998). The zona pellucida is removed from blastocysts by brief exposure to pronase. The inner cell masses can be isolated by immunosurgery or by mechanical separation, and are plated on mouse embryonic feeder layers, or in an appropriate culture system. Inner cell mass-derived outgrowths are then dissociated into clumps using calcium and magnesium-free phosphate-buffered saline (PBS) with 1 mM EDTA, using dispase, collagenase, or trypsin, or by mechanical dissociation with a micropipette. The dissociated cells are then replated for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli.

The ESC may be cultured under conditions that support the substantially undifferentiation growth of the primordial stem cells using any suitable cell culture techinique known in the art. For example, the ESCs may be grown on synthetic or purified extracellular matrix using methods standard in the art. Alternatively, the ESC may be grown on extracellular matrix that contains laminin or a growth-arrested murine or human feeder cell layer (e.g., a human foreskin fibroblast cell layer) and maintained in a serum-free growth environment.

Cell surface markers for ESC include, but are not limited to, alkine phosphatase, CD30, Cripto (TDGF-1), GCTM-2, Genesis, Germ cell nuclear factor, OCT-4/POU5F1, SSEA-3, SSEA-4, stem cell factor (SCF or c-kit ligand), TRA-1-60 and TRA-1-81.

Stem Cell Administration: Provided herein are methods of administering isolated somatic stem cells, such as MSC or ISC. The term "isolated" refers to a cell that has been removed from its in vivo location (e.g. bone marrow, neural tissue). In some cases, the isolated cell is substantially free from other substances (e.g., other cell types) that are present in its in vivo location. The stem cells of the present invention may be isolated or obtained using any technique, preferably known to those skilled in the art.

The somatic stem cells used in any of the methods of the invention may be obtained from any autologous or non-autologous (i.e., allogeneic or xenogeneic) human donor. For example, cells may be isolated from a donor subject. The somatic stem cells of the present invention may be administered to the treated subject using a variety of transplantation approaches.

Methods of culturing stem cells ex vivo are well known in the art. For example, see "Culture of Animal Cells—A Manual of Basic Technique" by Freshney, Wiley-Liss, N.Y. (1994), Third Edition, the teachings of which are hereby incorporated by reference.

Culture medium compositions typically include essential amino acids, salts, vitamins, minerals, trace metals, sugars, lipids and nucleosides. Cell culture medium supplies the necessary components to meet the nutritional needs for cells to grow in a controlled, artificial and in vitro environment. Nutrient formulations, pH, and osmolarity vary in accordance with parameters such as cell type, cell density, and the culture system employed. Many cell culture medium formulations are known in the art and a number of media are commercially available.

Once the culture medium is incubated with cells, it is known to those skilled in the art as "conditioned medium". Conditioned medium contains many of the original components of the medium, as well as a variety of cellular metabolites and secreted proteins, including, for example, biologically active growth factors, inflammatory mediators and other extracellular proteins.

Preconditioned media ingredients include, but are not limited to those described below. Additionally, the concentration of the ingredients is well known to one of ordinary skill in the art. See, for example, Methods For Preparation Of Media, Supplements and Substrate for Serum-free Animal Cell Cultures. The ingredients include amino-acids (both D and/or L-amino acids) such as glutamine, alanine, arginine, asparagine, cystine, glutamic acid, glycine, histidine, isoleucine, leucine, lysine, methionine, phenylalanine, proline, serine, threonine, tryptophan, tyrosine, and vatine and their derivatives; acid soluble subgroups such as thiamine, ascorbic acid, ferric compounds, ferrous compounds, purines, glutathione and monobasic sodium phosphates.

Additional ingredients include sugars, deoxyribose, ribose, nucleosides, water soluble vitamins, riboflavin, salts, trace metals, lipids, acetate salts, phosphate salts, HEPES, phenol red, pyruvate salts and buffers.

Other ingredients often used in media formulations include fat soluble vitamins (including A, D, E and K) steroids and their derivatives, cholesterol, fatty acids and lipids Tween 80, 2-mercaptoethanol pyramidines as well as a variety of supplements including serum (fetal, horse, calf, etc.), proteins (insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.). The media may or may not need to be supplemented with growth factors and other proteins such as attachment factors.

The term "transplantation," "cell replacement" or "grafting" are used interchangeably herein and refer to the introduction of the somatic stem cells of the present invention to target tissue such as areas of the SCI. The cells can be derived from the transplantation recipient or from an allogeneic or xenogeneic donor.

Conditions for successful transplantation include: (i) viability of the implant; (ii) retention of the graft at the site of transplantation; and (iii) minimum amount of pathological reaction at the site of transplantation.

For administration of the stem cells, an effective amount of the stem cells are diluted in suitable carriers. Exemplary carriers include phosphate buffered saline (PBS), culture medium and other buffered solutions.

The isolated stem cells may be administered by intravenous injection, by intraperitoneal injection or by preparing a cavity by surgical means to expose the spinal cord and then depositing the graft into the cavity. The cells may also be transplanted to a healthy region of the spinal cord. In some cases the exact location of the damaged tissue area may be unknown and the cells may be inadvertently transplanted to a healthy region. In other cases, it may be preferable to administer the cells to a healthy region, thereby avoiding any further damage to the injured region. Then following transplantation, the cells preferably migrate to the damaged area.

Since non-autologous stems cell may induce an immune reaction when administered to the body, steps may be necessary to decrease the likelihood of rejection of the stem cells. These steps include suppressing the recipient immune system or encapsulating the non-autologous stem cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag et al. Adv Drug Deliv Rev. 2000; 42: 29-64). Exemplary methods of preparing microcapsules include those made of alginate and alpha-phenoxycinnamylidene-acetylated poly(allylamine) (Lu et al., Biotechnol Bioeng. 2000, 70: 479-83) and photosensitive poly(allylamine alpha-cyanocinnamylideneacetate) (J. Microencapsul. 2000, 17: 245-51). In addition, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia. et al. Biomaterials. 2002 23: 849-56).

Other microcapsules are based on alginate, a marine polysaccharide (Sambanis et al., Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple et al., J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams Med Device Technol. 1999, 10: 6-9; Desai, Expert Opin Biol Ther. 2002, 2: 633-46).

Examples of immunosuppressive agents that may be administered in conjunction with the methods of the invention include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNFα. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

EXAMPLES

Restoration of Cognitive Function in Brain Injured Rats 12 Weeks after Traumatic Brain Injury Sprague Dawley rats were subjected to moderate parasagittal fluid-percussion brain injury using methods described in Atkins et al, *J Neurosci Res* 90, 1861-71 (2012). Adult male Sprague Dawley rats (280-300 g; Charles Rivers Laboratories) were anesthetized with 3% isoflurane, 70% $N_2O$, and 30% $O_2$ and received a 4.8-mm craniotomy (3.8 mm posterior to bregma, 2.5 mm lateral to the midline) over the right parietal cortex. Twenty-four hours after the craniotomy, the animals were re-anesthetized (3% isoflurane, 70% $N_2O$, and 30% $O_2$); immobilized with pancuronium bromide (1.0 mg/kg); and mechanically ventilated with 1% isoflurane, 70% $N_2O$, and 30% $O_2$. When physiological measurements had stabilized, the animals received a fluid-percussion pulse (1.8-2.2 atmospheres, 14-16 msec) or sham injury with the fluid-percussion brain injury device. Blood gases, blood pH, and mean arterial blood pressure were monitored for 30 min prior to the fluid percussion brain injury or sham surgery and for up to 1 hr post-injury to maintain normal levels. Injured and sham injured rats were coded such that the investigator assessing the behavior of the animals would not know their injury status.

2-(4-(2-(5-chlorothiophen-2-yl)-5-ethyl-6-methylpyrimidin-4-yl)amino)phenyl)acetic acid (Compound 33) was dissolved in 100% dimethylsulfoxide (DMSO) at 1 mg/ml and then diluted 20 fold into 0.9% sodium chloride (saline) with 2 molar equivalents of sodium hydroxide (0.258 mM) to yield a final concentration of Compound 33 at 0.05 mg/ml in 5% DMSO saline. Rats treated with vehicle received 5% DMSO in saline. Four treatment groups were studied; TBI rats treated with vehicle, TBI rats treated with Compound 33, sham rats treated with vehicle, and sham rats treated with Compound 33. Compound 33 and vehicle were delivered by intraperitoneal injection. Compound 33 was administered at a dose of 0.3 mg/kg. Rats did not receive the vehicle or Compound 33 right after surgery, but were allowed to recover for 12 weeks prior to the administration. At 12 weeks after surgery, the rats were administered either vehicle or Compound 33 only 30 minutes prior to training on the water maze test.

Twelve weeks after surgery, rats were tested for cognitive ability using the water maze test. Animals received vehicle or Compound 33 (0.3 mg/kg, i.p.) 30 min prior to water maze training. The circular pool (122 cm diameter, 60 cm deep) was filled with opaque water at 24° C. and surrounded by distinct, invariant extramaze cues. An escape platform, 9.3 cm in diameter, was submerged 1.5 cm below the water surface. Animals received four 60 s acquisition trials per day for 4 days with inter-trial intervals of 4 min. If the rat failed to navigate to reach the platform within 60 s, it was guided to the platform and remained on the platform for 10 s. Path length to reach the platform, escape latency, and swim speed were analyzed with EthoVision software (Noldus Information Technology). After 4 training days, a probe trial (60 s duration) was given with the platform removed and no drug treatment was given prior to the probe trial.

During acquisition, TBI animals failed to display progressive learning. Even on the 4th day of training, TBI animals treated with vehicle had significantly longer escape latencies and path lengths as compared to sham animals treated with vehicle. In contrast, TBI animals treated with Compound 33 displayed a progressive decrease in escape latency and path length to reach the hidden platform and these indices of learning were comparable to sham animals treated with vehicle or Compound 33 on the 4th day of acquisition. 24 h after the last acquisition trial, animals were tested for retention during a probe trial with the platform removed. On this day to test recall, animals did not receive either Compound 33 or vehicle. TBI animals that had been treated with vehicle on the acquisition days spent less time in the target quadrant as compared to Compound 33-treated TBI animals or sham animals treated with vehicle or Compound 33 on the acquisition days.

To assess working memory in TBI animals, a working memory version of the water maze task was used on week 14 post-surgery. At 30 min prior to testing, animals received Compound 33 (0.3 mg/kg) or vehicle. Four paired trials were given each day for 2 days with inter-trial intervals of 4 min. Rats received vehicle or Compound 33 at 30 minutes prior to water maze testing. Trial duration was 60 s. The hidden platform remained invariant in location for each pair of trials. Upon reaching the platform, the animal remained on the platform for 10 s. After a 5 s delay, the animal was released into the water maze to again search for the hidden platform in the same location. Escape latency differences between the first location trial and subsequent match trial were measured. There was a significant impairment in working memory in TBI animals treated with vehicle as compared to sham animals, and this deficit was rescued by Compound 33 treatment of TBI animals.

Human Clinical Trial to Demonstrate Pro-cognitive Benefit in Subjects with Traumatic Brain Injury The selective PDE4B inhibitor is assessed in a 4 week, double-blind, randomized, multiple dose, placebo controlled, cross-over study to examine pro-cognitive benefit in otherwise healthy male or female subjects who have sustained a TBI 1-5 years previously and continue to have measurable cognitive impairment. The TBI may or may not have resulted in hospitalization. To be included in the study, subjects will have sustained a closed or open head injury resulting in moderate-to-severe impairment of consciousness. Impairment of consciousness will have been assessed using the Glasgow Coma Scale (GCS), Rancho Los Amigos, or similar clinical scale. Subjects included in the study will have sustained a TBI that resulted in impairment of consciousness of GCS <9 indicating severe loss of consciousness, or GCS <13 indicating moderate loss of consciousness. The TBI will have resulted in measureable cognitive impairment 1-5 years after injury. The advantage of the crossover design is that each subject will act as their own control and fewer subjects will be required than a between-group design. In the first stage of the trial, subjects are randomized to receive either the PDE4B inhibitor or placebo for 4 weeks. After a two week washout, subjects crossover to the second stage of the trial in which those that previously received the PDE4B inhibitor now receive placebo for 4 weeks. Correspondingly, those that received placebo previously cross over to receive the PDE4B inhibitor for 4 weeks. The primary outcome measure is assessment of cognitive function.

Further Embodiments of the Disclosure

1. A method of improving cognitive function in a mammalian subject with cognitive impairment, the method comprising administering to the subject a selective PDE4 B inhibitor, in an amount effective to improve cognitive function.
2. Use of a selective PDE4 B inhibitor to improve cognitive function in a mammalian subject with cognitive impairment.
3. A method of improving cognitive function in a mammalian subject with cognitive impairment, the method comprising contacting cells of the subject with a selective PDE4 B inhibitor, in an amount effective to improve cognitive function, wherein the cells are brain cells, spinal cells, and/or neural cells.
4. The method or use according to any one of paragraphs 1-3, wherein the selective PDE4 B inhibitor is formulated in a composition that includes a pharmaceutically acceptable carrier.
5. The method or use according to any one of paragraphs 1-4, wherein the subject is a human.
6. The method or use according to any one of paragraphs 1-5, wherein the cognitive impairment followed a traumatic brain injury.
7. The method or use according to paragraph 6, wherein the traumatic brain injury is a closed traumatic brain injury.
8. The method or use according to paragraph 7, wherein the traumatic brain injury is a penetrating traumatic brain injury.
9. The method or use according to paragraph 7 or 8, wherein the traumatic brain injury results from proximity or exposure to an explosive blast or blast wind.
10. The method or use according to paragraph 6, wherein the traumatic brain injury results from one or more concussion events, or chronic traumatic encephalopathy (CTE).
11. The method or use according to paragraph 10, wherein the one or more concussion events include repeated head trauma from sports or athletics or a vehicular accident.
12. The method or use according to paragraph 6, wherein the traumatic brain injury resulted from a fall or from child or domestic abuse.
13. The method or use according to any one of paragraphs 1-5, wherein the cognitive impairment followed a brain hypoxia event.
14. The method or use according to paragraph 13, wherein the hypoxia event resulted from a cardiac arrest, a myocardial infarction, a stroke, a near suffocation, a near drowning, during general anesthesia, during cardiac surgery, or during open heart surgery.
15. The method or use according to paragraph 14, wherein the hypoxia event occurred prenatally or perinatally.
16. The method or use according to any one of paragraphs 1-15, wherein the improvement to cognitive function comprises improved short term memory.
17. The method or use according to any one of paragraphs 1-16, wherein the improvement to cognitive function comprises improved long term memory.
18. The method or use according to any one of paragraphs 1-17, wherein the improvement to cognitive function comprises improved attention span.
19. The method or use according to any one of paragraphs 1-18, wherein the improvement to cognitive function comprises improved working memory.
20. The method or use according to any one of paragraphs 1-19, wherein the improvement in cognitive function comprises improvement with at least one parameter selected from attention span, judgment, processing speed, distractability, abstract reasoning, planning, problem-solving, working memory, and multi-tasking.
21. The method or use according to any one of paragraphs 6-20, wherein the cognitive impairment is measurable or has persisted past the acute stage of brain injury, and wherein administration of or contacting with the selective PDE4 B inhibitor is initiated during a subsequent chronic stage following the brain injury.
22. The method or use according to any one of paragraphs 6-20, wherein the cognitive impairment is measurable or has persisted for at least two, at least four, or at least six weeks following a brain injury, and wherein administration of or contacting with the selective PDE4 B inhibitor is initiated or repeated at least two, at least four, or at least six weeks following the brain injury.
23. The method or use according to any one of paragraphs 6-20, wherein the cognitive impairment is measurable or has persisted for at least two, at least four, or at least six months following a brain injury, and wherein administration of or contacting with the selective PDE4 B inhibitor is initiated or repeated at least two, at least four, or at least six months following the brain injury.
24. The method or use according to any one of paragraphs 6-20, wherein the cognitive impairment is measurable or has persisted for at least 1, 2, 3, 4, 5, 6, 8, or 10 years following a brain injury, and wherein administration of or contacting with the selective PDE4 B inhibitor is initiated or repeated at least 1, 2, 3, 4, 5, 6, 8, or 10 years following the brain injury.
25. The method or use according to any one of paragraphs 6-20, wherein the brain injury has been treated with a first therapy selected from tissue plasminogen activator, urokinase, and progesterone, and wherein administration of or contacting with the selective PDE4B inhibitor is initiated or repeated following cessation of the first therapy.
26. The method or use according to any one of paragraphs 1, 2, and 4-25, wherein the selective PDE4 B inhibitor is administered orally or intravenously.
27. The method or use according to any one of paragraphs 1-25, wherein the selective PDE4 B inhibitor is formulated for and/or administered intracranially, intracerebrally, intracerebroventricularly, epidurally, or intrathecally.
28. The method or use according to any one of paragraphs 1-27, wherein the selective PDE4 B inhibitor is administered to the subject or contacted to the cells of the subject for at least 2 weeks.
29. The method or use according to any one of paragraphs 1-28, wherein the selective PDE4 B inhibitor is administered to the subject or contacted to the cells of the subject for not more than 6 months or 1 year.
30. The method or use according to any one of paragraphs 1-29, wherein the selective PDE4 B inhibitor is administered to the subject or contacted to the cells after or concurrent to rehabilitation therapy.
31. The method or use of any one of paragraphs 1-30, wherein the selective PDE4 B inhibitor has a structure of formula (I):

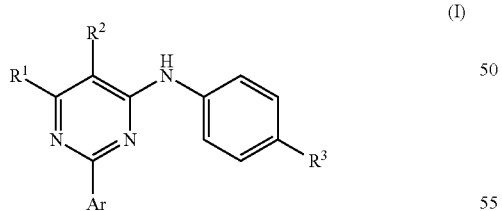

wherein
R$^1$ and R$^2$ are each independently C$_1$-C$_4$ alkyl or C$_2$-C$_4$ alkenyl;
R$^3$ is (CH$_2$)$_n$CO$_2$H;
n is 0, 1, or 2;
Ar is an optionally substituted aryl or heteroaryl;
or a salt, ester, or solvate thereof.
32. The method or use of paragraph 31, wherein R$^1$ and R$^2$ are each C$_1$-C$_4$ alkyl.
33. The method or use of paragraph 32, wherein R$^1$ is Me and R$^2$ is Et.
34. The method or use of any one of paragraphs 31 to 33, wherein n is 0.
35. The method or use of any one of paragraphs 31 to 33, wherein n is 1.
36. The method or use of any one of paragraphs 31 to 35, wherein Ar is optionally substituted aryl.
37. The method or use of paragraph 36, wherein Ar is phenyl.
38. The method or use of any one of paragraphs 31 to 35, wherein Ar is optionally substituted thiophenyl.
39. The method or use of paragraph 38, wherein Ar is optionally substituted 2-thiophenyl.
40. The method or use of paragraph 38, wherein Ar is optionally substituted 3-thiophenyl.
41. The method or use of any one of paragraphs 38 to 40, wherein the thiophenyl is substituted with one or more of Cl, F, CH$_3$, and SCH$_3$.
42. The method or use of any one of paragraphs 38 to 40, wherein the thiophenyl is unsubstituted.
43. The method or use of any one of paragraphs 1-30, wherein the PDE4 B inhibitor is selected from the group consisting of

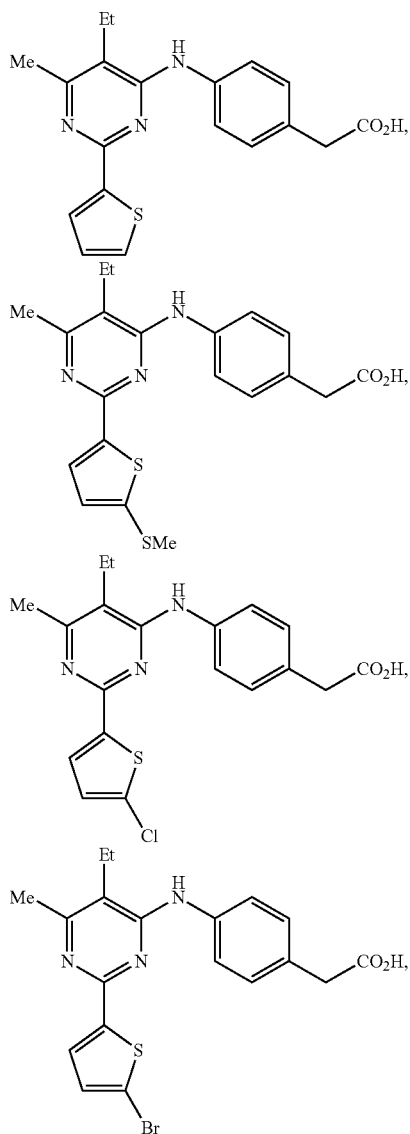

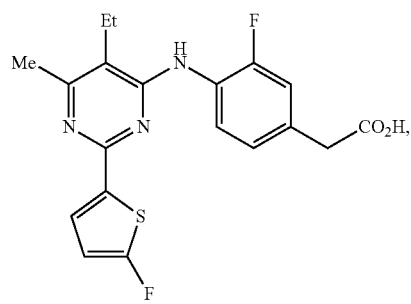
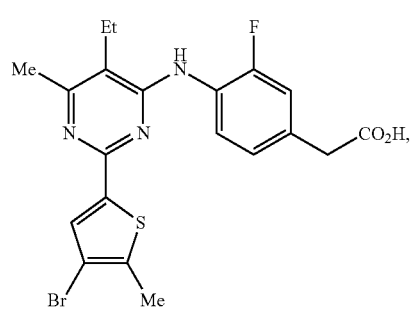
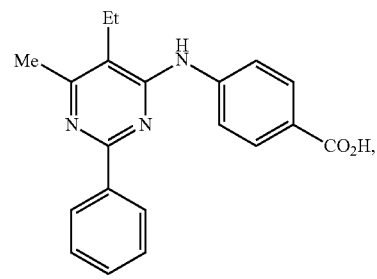
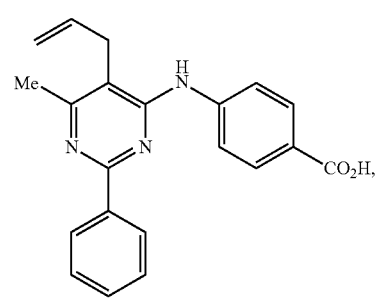
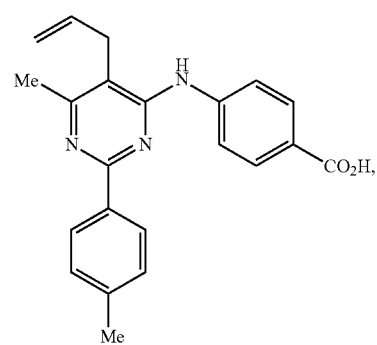
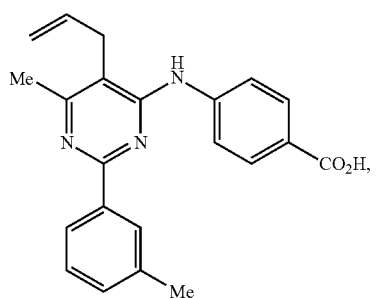
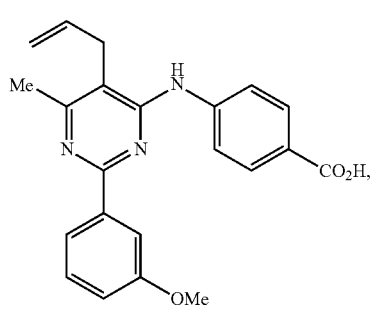
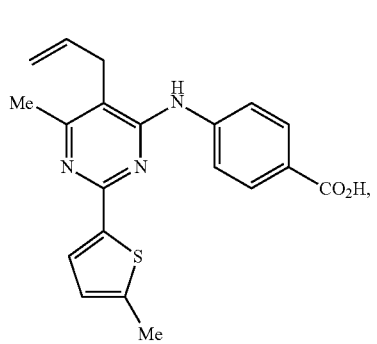
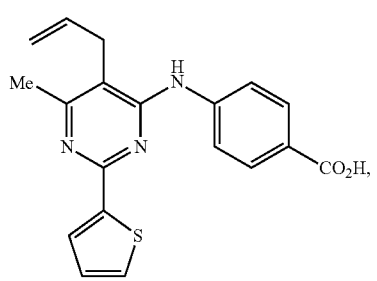
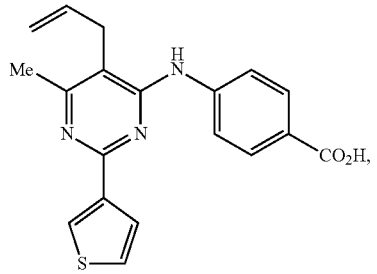

-continued

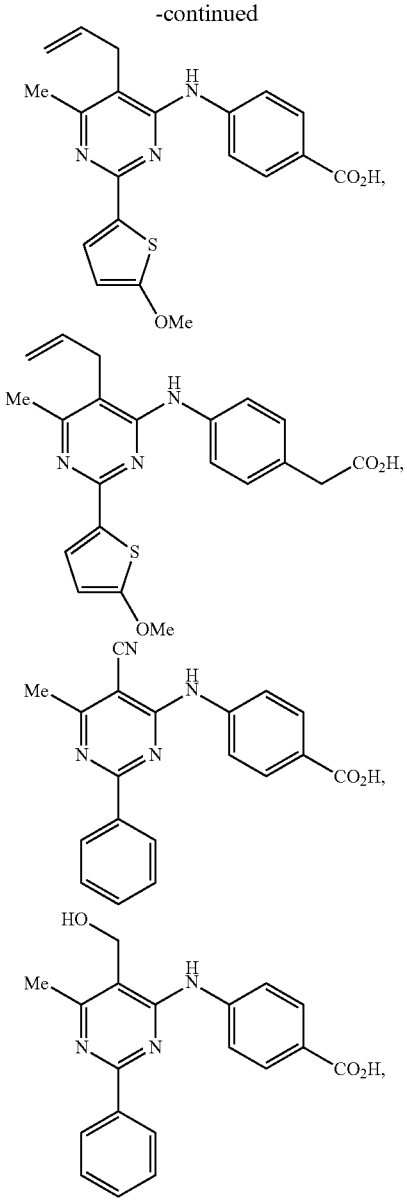

or a salt, ester, or solvate thereof.

44. The method or use of any one of paragraphs 1-30, wherein the selective PDE4 B inhibitor is

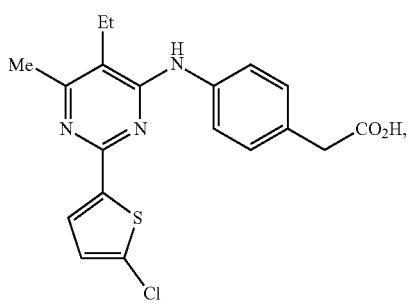 [SMILES: CCc1c(C)nc(-c2ccc(Cl)s2)nc1Nc1ccc(CC(=O)O)cc1]

or a salt, ester or solvate thereof.

45. A method of improving one or more of motor function, sensory function and paralysis in a mammalian subject suffering from a spinal cord injury comprising administering to the subject an effective amount of a selective PDE4 B inhibitor to improve one or more of motor function, sensory function and paralysis.

46. Use of a selective PDE4 B inhibitor to improve one or more of motor function, sensory function and paralysis in a mammalian subject suffering from a spinal cord injury.

47. A method of improving one or more of motor function, sensory function and paralysis in a mammalian subject suffering from a spinal cord injury comprising contacting cells of the subject with an effective amount of a selective PDE4 B inhibitor to improve one or more of motor function, sensory function and paralysis, wherein the cells are one or more of spinal cells and neural cells.

48. The method or use of any one of paragraphs 45 to 47, wherein the selective PDE4 B inhibitor is formulated in a composition that includes a pharmaceutically acceptable carrier.

49. The method or use of any one of paragraphs 45 to 48, wherein the subject is a human.

50. The method or use of any one of paragraphs 45 to 49, further comprising transplanting cells in the spinal cord.

51. The method or use of paragraph 50, wherein the cells are stem cells or glial cells.

52. The method or use of paragraph 51, wherein the cells are Schwann cells.

53. The method or use of any one of paragraphs 45 to 52, wherein the sensory function impairment, motor function impairment, or paralysis is measurable or has persisted for at least two, at least four, or at least six weeks following the spinal cord injury, and wherein administration of or contacting with the selective PDE4 B inhibitor is initiated at least two, at least four, or at least six weeks following the spinal cord injury.

54. The method or use of any one of paragraphs 45 to 52, wherein the sensory function impairment, motor function impairment, or paralysis is measurable or has persisted for at least two, at least four, or at least six months following the spinal cord injury, and wherein administration of or contacting with the selective PDE4 B inhibitor is initiated at least two, at least four, or at least six months following the spinal cord injury.

55. The method or use of any one of paragraphs 45 to 52, wherein the sensory function impairment, motor function impairment, or paralysis is measurable or has persisted for at least 1, 2, 3, 4, 5, 6, 8, or 10 years following the spinal cord injury, and wherein administration of or contacting with the selective PDE4 B inhibitor is initiated at least 1, 2, 3, 4, 5, 6, 8, or 10 years following the spinal cord injury.

56. The method or use of any one of paragraphs 45 to 55, wherein the selective PDE4 B inhibitor has a structure of formula (I):

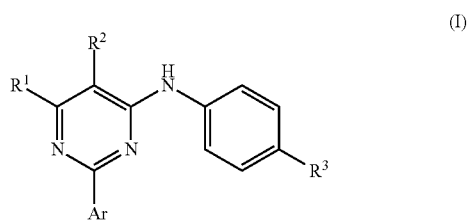

wherein $R^1$ and $R^2$ are each independently $C_1$-$C_4$ alkyl or $C_2$-$C_4$ alkenyl;

$R^3$ is $(CH_2)_n CO_2 H$;

n is 0, 1, or 2;

Ar is an optionally substituted aryl or heteroaryl;

or a salt, ester, or solvate thereof.

57. The method or use of paragraph 56, wherein $R^1$ and $R^2$ are each $C_1$-$C_4$ alkyl.
58. The method or use of paragraph 57, wherein $R^1$ is Me and $R^2$ is Et.
59. The method or use of any one of paragraphs 56 to 58, wherein n is 0.
60. The method or use of any one of paragraphs 56 to 58, wherein n is 1.
61. The method or use of any one of paragraphs 56 to 60, wherein Ar is optionally substituted aryl.
62. The method or use of paragraph 61, wherein Ar is phenyl.
63. The method or use of any one of paragraphs 56 to 60, wherein Ar is optionally substituted thiophenyl.
64. The method or use of paragraph 63, wherein Ar is optionally substituted 2-thiophenyl.
65. The method or use of paragraph 63, wherein Ar is optionally substituted 3-thiophenyl.
66. The method or use of any one of paragraphs 63 to 65, wherein the thiophenyl is substituted with one or more of Cl, F, $CH_3$, and $SCH_3$.
67. The method or use of any one of paragraphs 63 to 65, wherein the thiophenyl is unsubstituted.
68. The method or use of any one of paragraphs 45 to 55, wherein the PDE4 B inhibitor is selected from the group consisting of

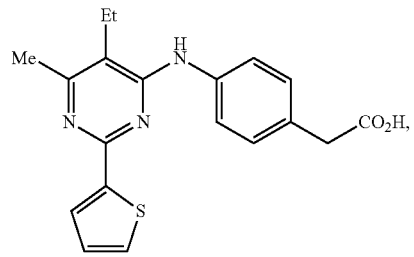

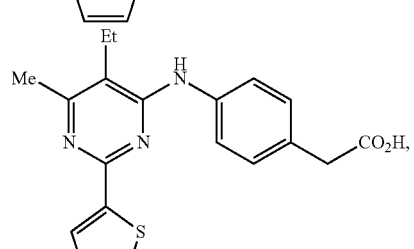

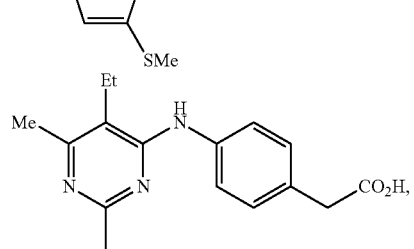

-continued

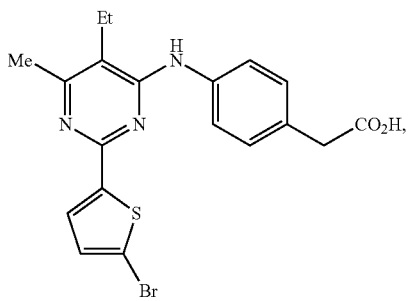

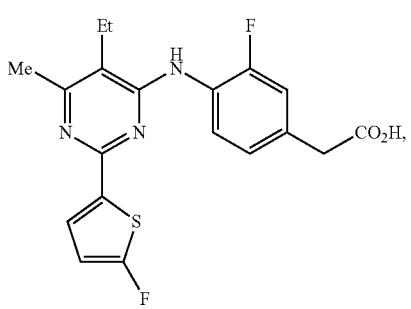

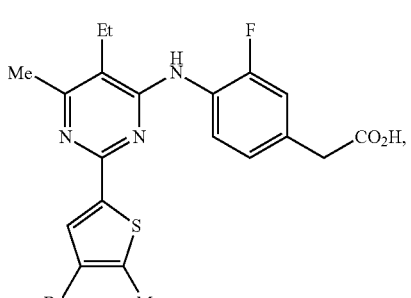

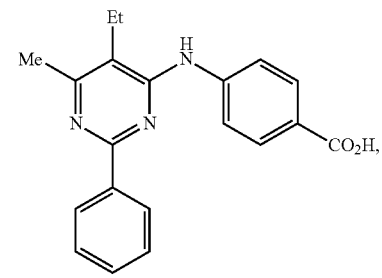

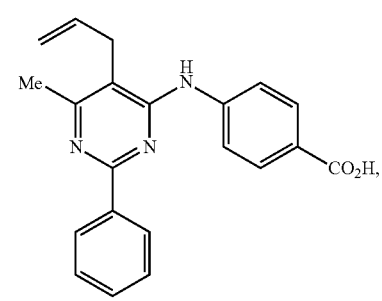

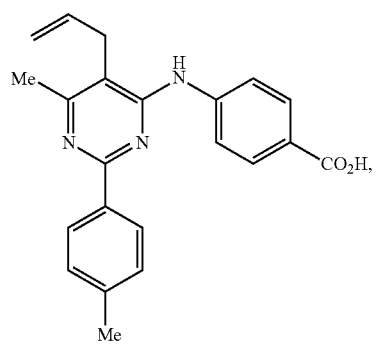
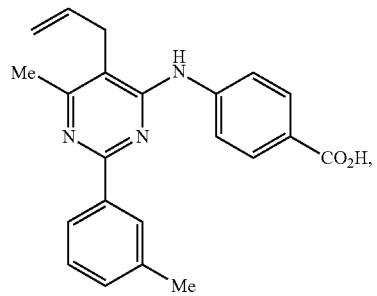
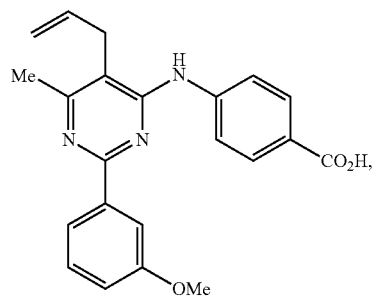
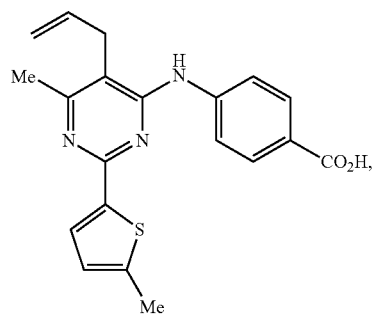
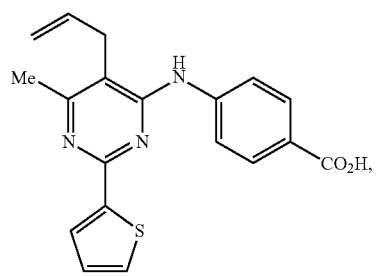
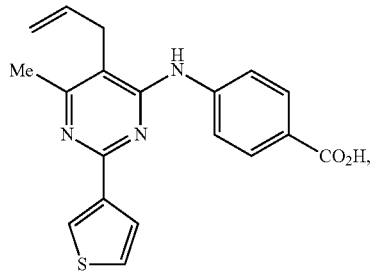
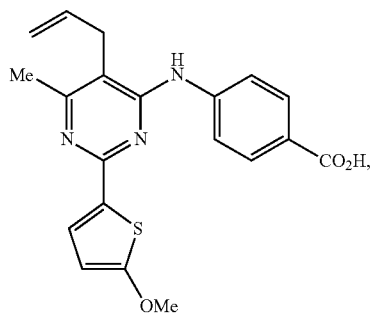
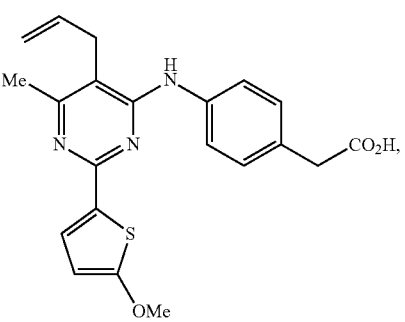
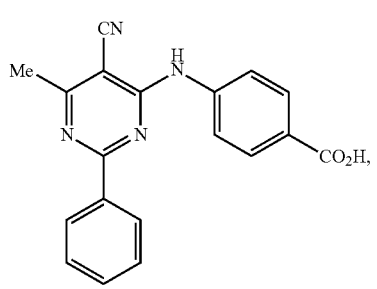
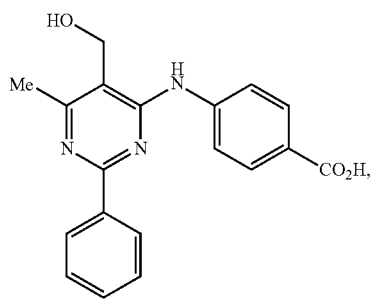
or a salt, ester, or solvate thereof.
69. The method or use of any one of paragraphs 45 to 55, wherein the selective PDE4 B inhibitor is

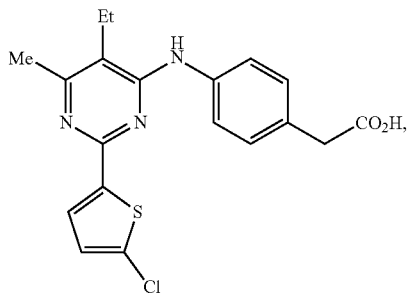

or a salt, ester or solvate thereof.

70. A method of improving cognitive function comprising:

examining a human subject who has had a traumatic brain injury to determine if cognitive impairment exists; and prescribing or administering to a subject identified as having cognitive impairment a composition that comprises a selective PDE4 B inhibitor and a pharmaceutically acceptable diluents, excipient, or carrier.

71. A method of improving cognitive function comprising:

examining a human subject who has had a traumatic brain injury to determine if cognitive impairment exists; and contacting brain cells of a subject identified as having cognitive impairment with a selective PDE4 B inhibitor.

72. The method of paragraph 70 or 71, wherein the examining is performed after treatment for the traumatic brain injury has ceased.

73. The method of any one of paragraphs 70 to 72, wherein the examining comprise assessing the subject using the Glasgow Coma Scale or Rancho Los Amigos scale.

74. The method of any one of paragraphs 70-73, wherein the selective PDE4 B inhibitor has a structure of formula (I):

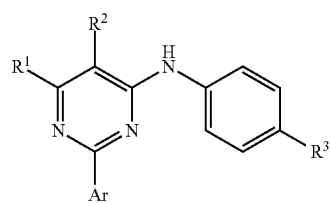

wherein $R^1$ and $R^2$ are each independently $C_1$-$C_4$ alkyl or $C_2$-$C_4$ alkenyl;

$R^3$ is $(CH_2)_n CO_2 H$;

n is 0, 1, or 2;

Ar is an optionally substituted aryl or heteroaryl;

or a salt, ester, or solvate thereof.

What is claimed is:

1. A method of improving cognitive function in a mammalian subject with cognitive impairment due to a traumatic brain injury, the method comprising administering to the subject a selective PDE4 B inhibitor, in an amount effective to improve cognitive function, wherein the selective PDE4 B inhibitor has a structure of formula (I):

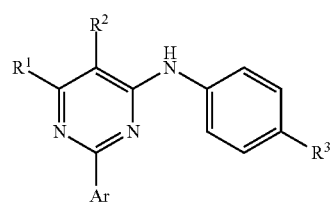

wherein $R^1$ is methyl and $R^2$ is ethyl;

$R^3$ is $CH_2 CO_2 H$;

Ar is an optionally substituted thienyl; or a salt, ester, or solvate thereof.

2. The method of claim 1, wherein the traumatic brain injury results from one or more concussion events, or chronic traumatic encephalopathy (CTE).

3. The method of claim 1, wherein the improvement to cognitive function comprises improved short term memory, improved long term memory, improved attention span, or improved working memory.

4. The method of claim 1, wherein the cognitive impairment is measurable or has persisted past the acute stage of brain injury, or wherein the administration of the selective PDE4 B inhibitor is initiated during a subsequent chronic stage following the brain injury.

5. The method of claim 1, wherein the cognitive impairment is measurable or has persisted for at least six weeks following a brain injury.

6. The method of claim 1, wherein administration of the selective PDE4 B inhibitor is initiated at least six weeks following the brain injury.

7. The method of claim 6, wherein administration of the selective PDE4 B inhibitor is initiated at least six months following the brain injury.

8. The method of claim 1, wherein the selective PDE4 B inhibitor is administered for at least 2 weeks.

9. The method of claim 1, wherein the thiophenyl is substituted with one or more of Cl, F, $CH_3$, and $SCH_3$.

10. The method of claim 1, wherein the selective PDE4 B inhibitor has a structure selected from the group consisting of

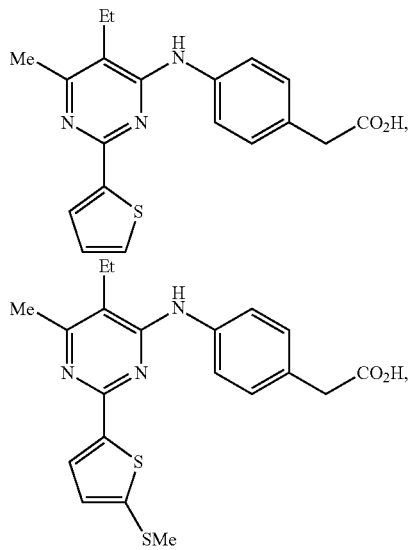

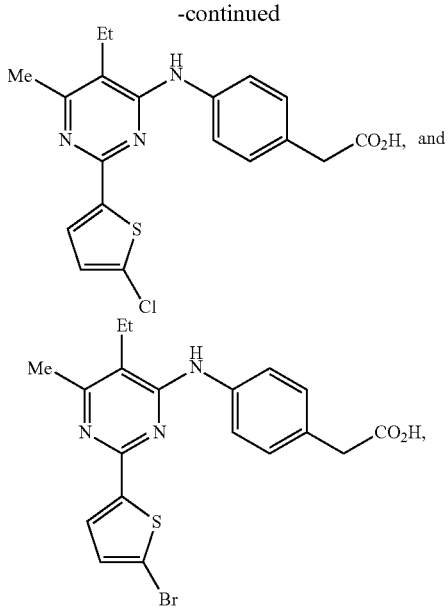

or a salt, ester, or solvate thereof.

11. The method of claim 1, wherein the selective PDE4 B inhibitor is a compound having a structure

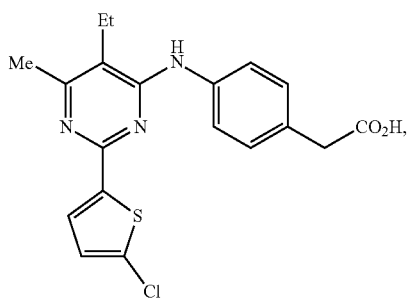

or a salt, ester or solvate thereof.

12. The method of claim 1, wherein the subject is human.

13. A method of improving cognitive function in a mammalian subject with cognitive impairment that followed a traumatic brain injury, the method comprising contacting brain cells of the subject with a selective PDE4 B inhibitor, in an amount effective to improve cognitive function, wherein the selective PDE4 B inhibitor has a structure of formula (I):

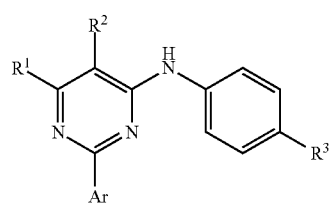

wherein
$R^1$ is methyl and $R^2$ is ethyl;
$R^3$ is $CH_2CO_2H$;
Ar is an optionally substituted thienyl;
or a salt, ester, or solvate thereof.

14. The method of claim 13, wherein the improvement to cognitive function comprises improved short term memory, improved long term memory, improved attention span, or improved working memory.

15. The method of claim 13, wherein the cognitive impairment is measurable or has persisted for at least six weeks following a brain injury.

16. The method of claim 13, wherein administration of the selective PDE4 B inhibitor is initiated at least six weeks following the brain injury.

17. The method of claim 13, wherein the cognitive impairment is measurable or has persisted past the acute stage of brain injury, or wherein the contacting of the selective PDE4 B inhibitor is initiated during a subsequent chronic stage following the brain injury.

18. The method of claim 13, wherein the PDE4 B inhibitor is selected from the group consisting of

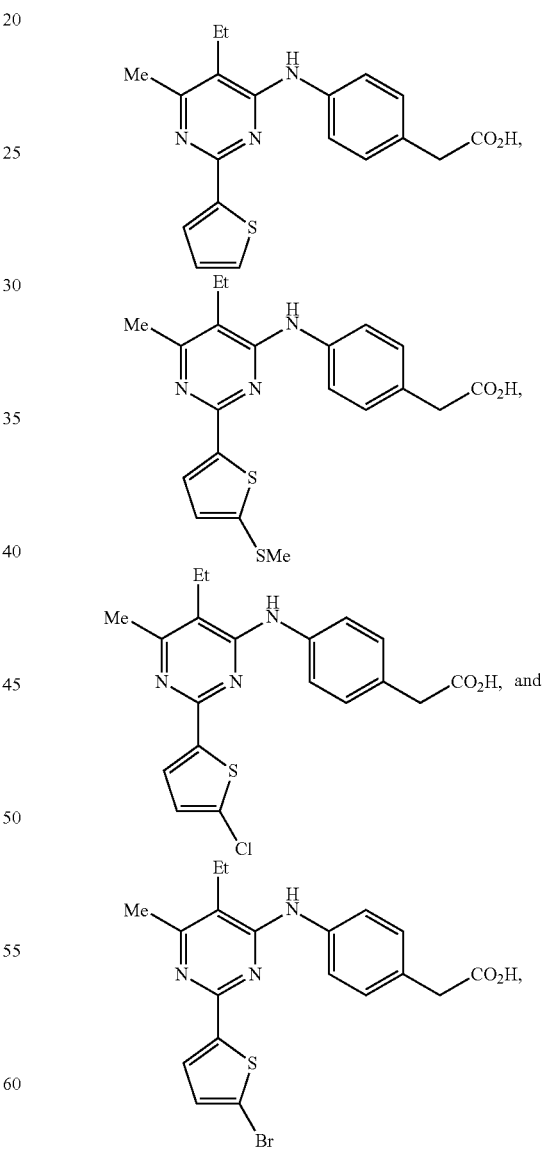

or a salt, ester, or solvate thereof.

19. The method of claim 13, wherein the selective PDE4 B inhibitor is a compound having a structure

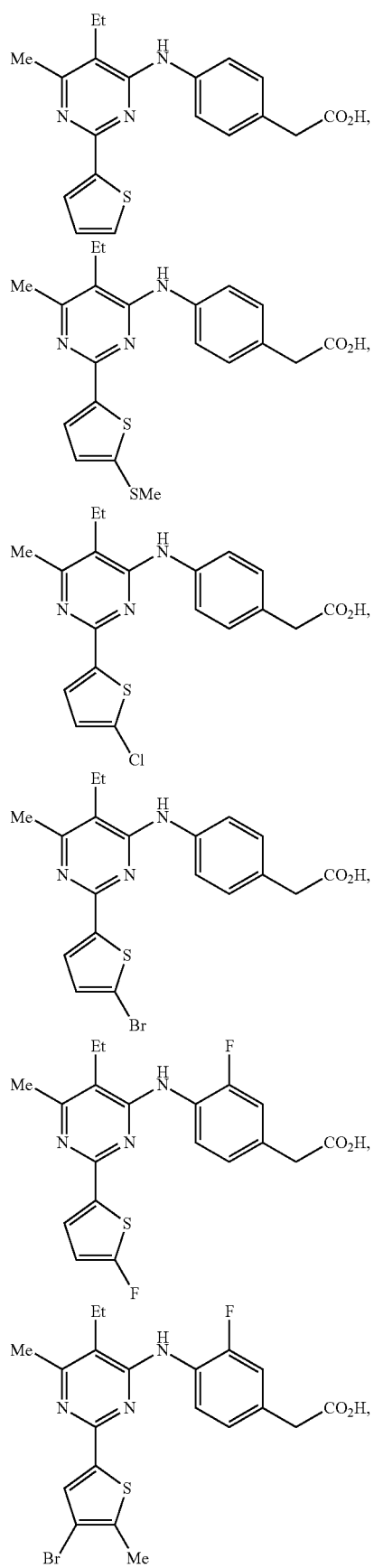
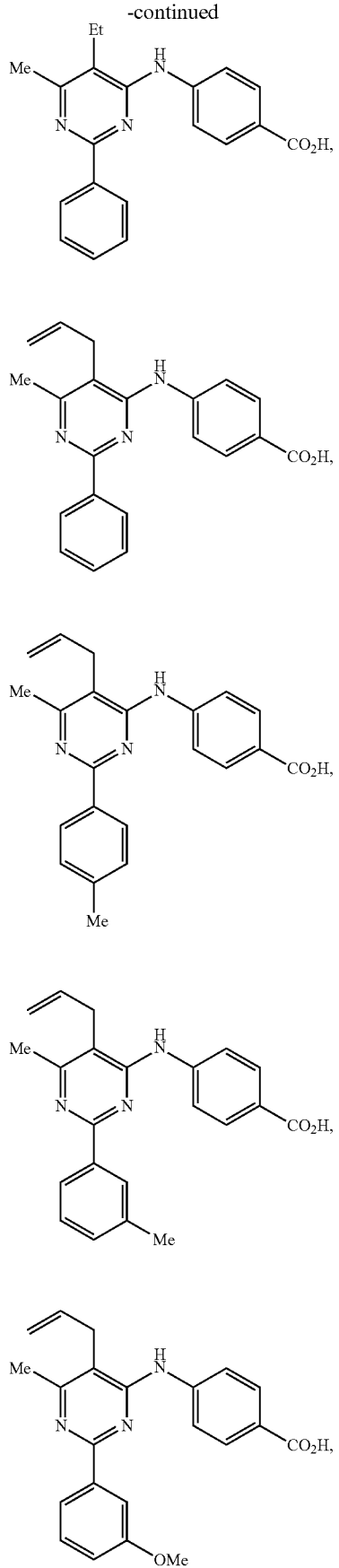

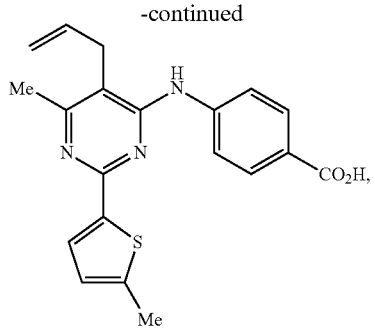

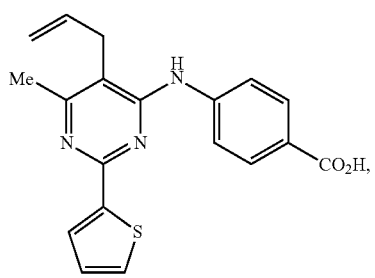

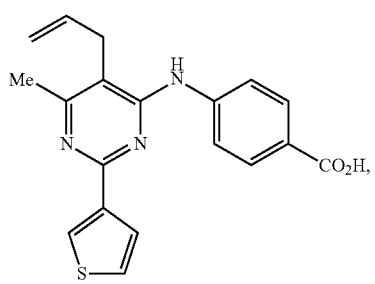

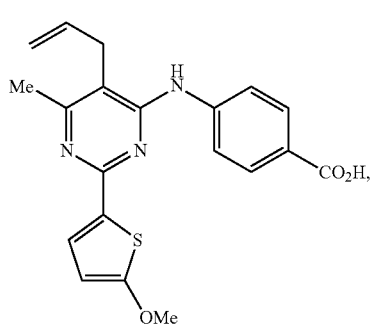

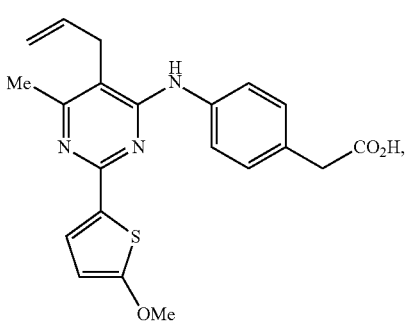

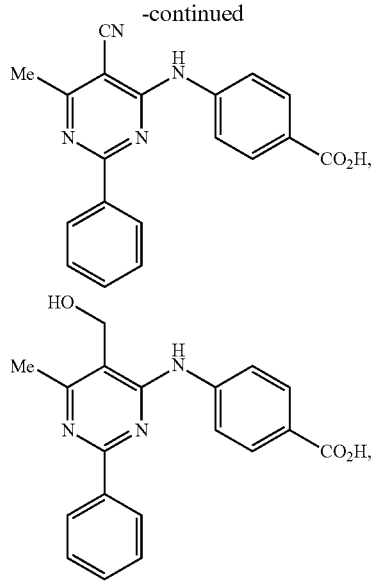

or a salt, ester or solvate thereof.

20. The method of claim 13, wherein the subject is human.

21. A method of improving cognitive function comprising:
examining a human subject following cessation of a treatment of the subject for a traumatic brain injury to determine if cognitive impairment exists following the treatment; and
for the subject identified by the examining as having cognitive impairment, administering to the subject, or contacting brain cells of the subject with a selective PDE4 B inhibitor having a structure of formula (I):

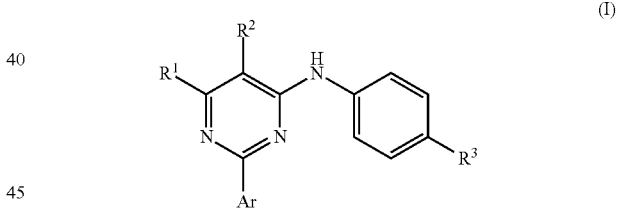

wherein
$R^1$ is methyl and $R^2$ is ethyl;
$R^3$ is $CH_2CO_2H$;
Ar is an optionally substituted thienyl;
or a salt, ester, or solvate thereof.

22. The method of claim 21, wherein the PDE4 B inhibitor is selected from the group consisting of

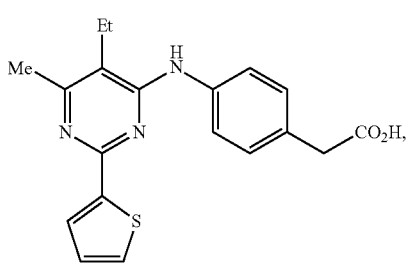

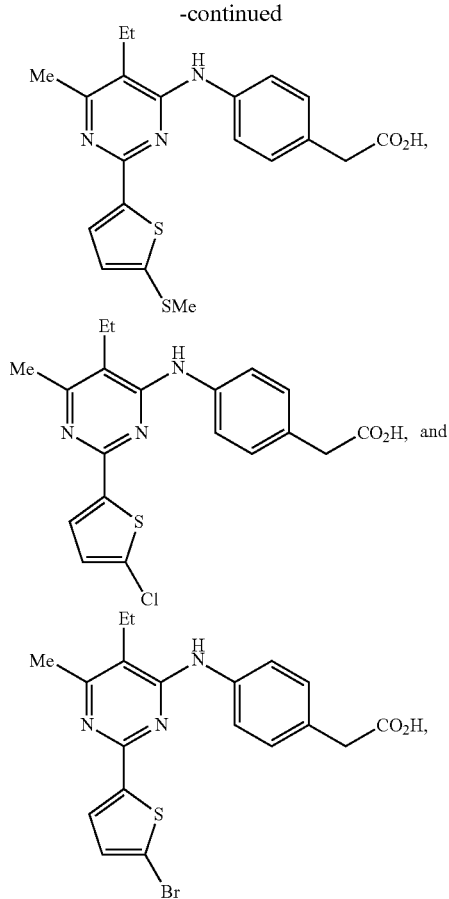

or a salt, ester, or solvate thereof.

23. The method of claim 21, wherein the selective PDE4 B inhibitor is a compound having a structure

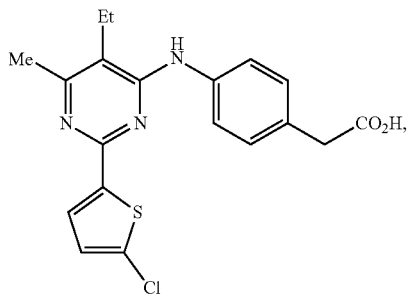

or salt, ester or solvate thereof.

24. A method of improving cognitive function in a mammalian subject with cognitive impairment due to a traumatic brain injury, the method comprising administering to the subject a selective PDE4 B inhibitor, in an amount effective to improve cognitive function, wherein the selective PDE4 B inhibitor is selected from the group consisting of:

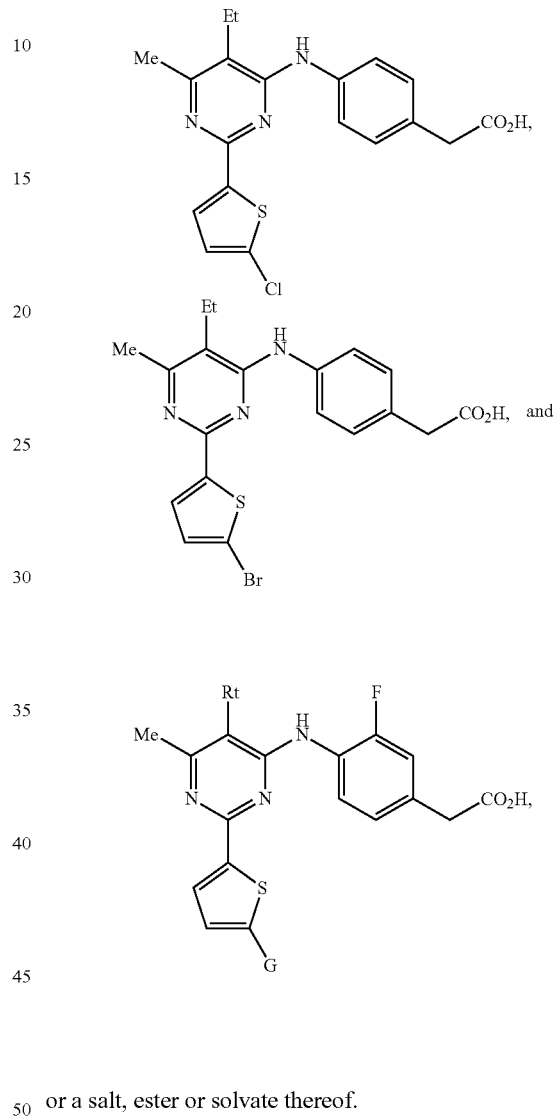

or a salt, ester or solvate thereof.

* * * * *

UNITED STATES PATENT AND TRADEMARK OFFICE
CERTIFICATE OF CORRECTION

| | | |
|---|---|---|
| PATENT NO. | : 8,865,723 B2 | |
| APPLICATION NO. | : 13/799505 | |
| DATED | : October 21, 2014 | |
| INVENTOR(S) | : Mark E. Gurney et al. | |

It is certified that error appears in the above-identified patent and that said Letters Patent is hereby corrected as shown below:

<u>In the Claims:</u>

At Column 61, lines 1-65, delete compound on the attached page

Signed and Sealed this
Eighth Day of March, 2016

Michelle K. Lee
*Director of the United States Patent and Trademark Office*

CERTIFICATE OF CORRECTION (continued)
U.S. Pat. No. 8,865,723 B2

Column 61, lines 1-65, cont'd

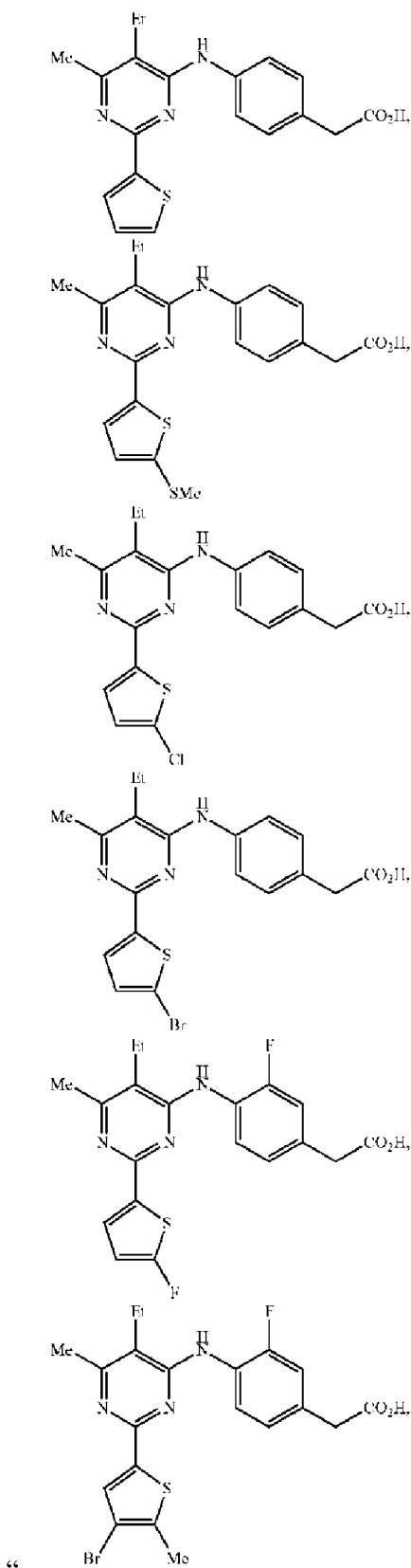

CERTIFICATE OF CORRECTION (continued)
U.S. Pat. No. 8,865,723 B2

In the Claims:

Column 61, lines 1-65, cont'd, and insert

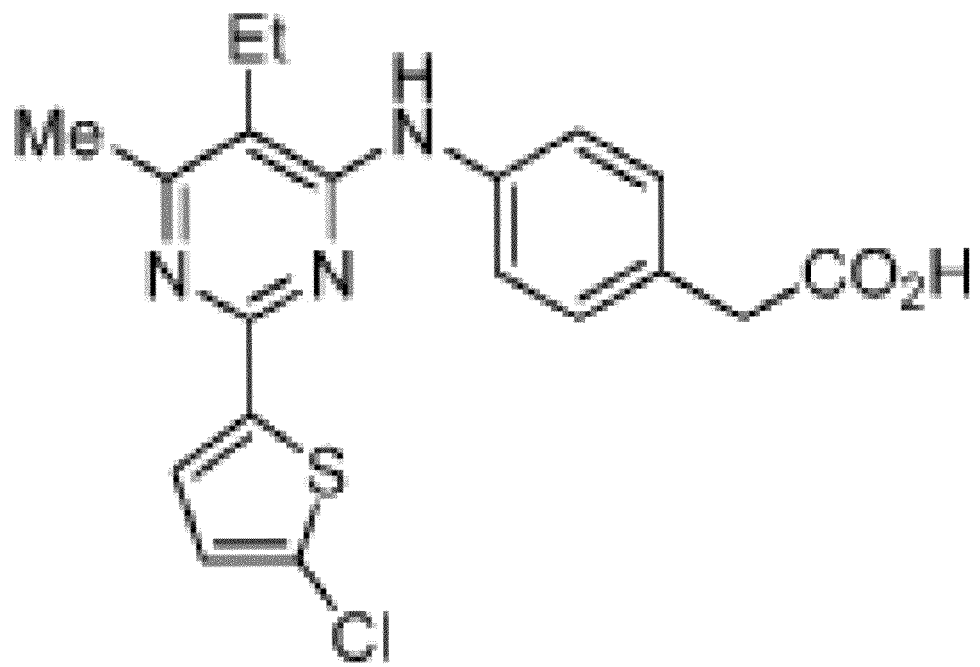

-- --

CERTIFICATE OF CORRECTION (continued)
U.S. Pat. No. 8,865,723 B2

In the Claims:

At Column 62, lines 1-65, delete compound on the attached page

Column 62, lines 1-65, cont'd
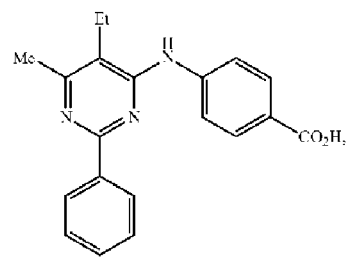
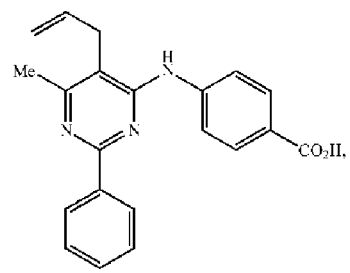
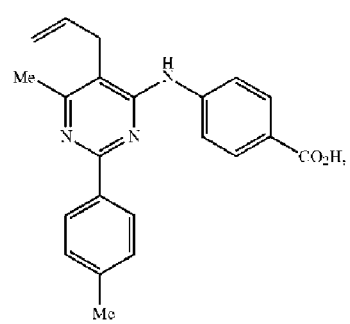
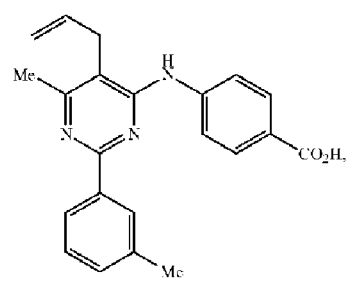
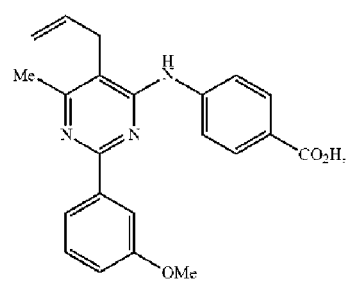
" "

CERTIFICATE OF CORRECTION (continued)
U.S. Pat. No. 8,865,723 B2

In the Claims:

At Column 63, lines 1-65, delete compound on the attached page

Column 63, lines 1-65 cont'd
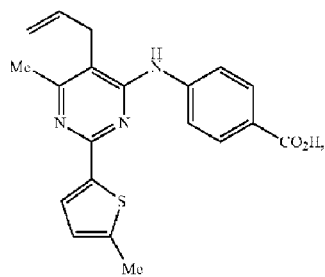
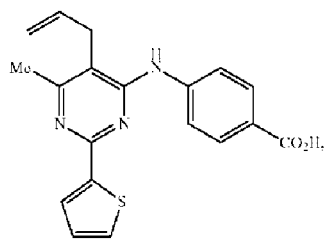
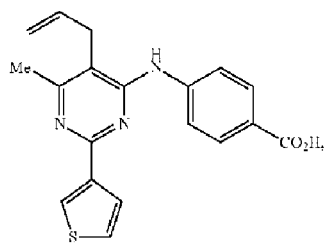
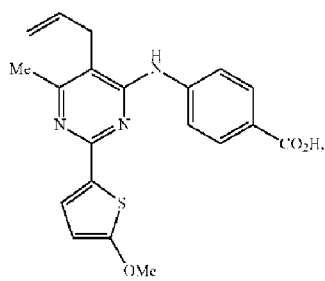
" 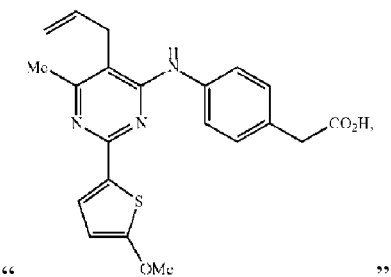 "

CERTIFICATE OF CORRECTION (continued)
U.S. Pat. No. 8,865,723 B2

Page 8 of 8

In the Claims:

At Column 64 lines 1-23, delete

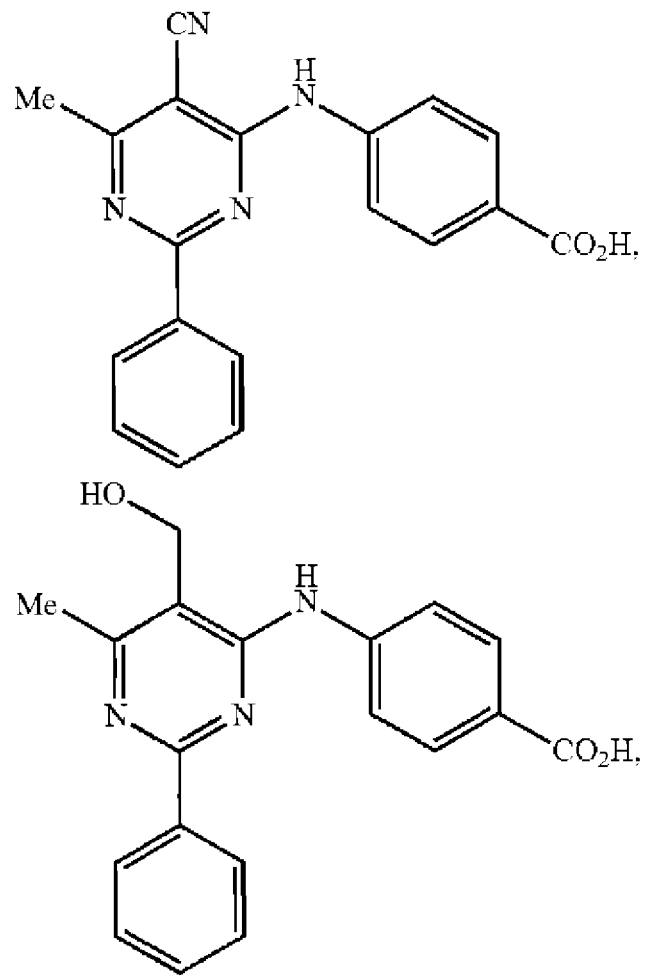

"                                                                    "